United States Patent
Kulik

(10) Patent No.: US 9,708,154 B2
(45) Date of Patent: Jul. 18, 2017

(54) OFF-ROAD ROLLING FILM VISION SYSTEM

(71) Applicant: Mark Kulik, Hayward, CA (US)

(72) Inventor: Mark Kulik, Hayward, CA (US)

( * ) Notice: Subject to any disclaimer, the term of this patent is extended or adjusted under 35 U.S.C. 154(b) by 0 days.

(21) Appl. No.: 14/543,794

(22) Filed: Nov. 17, 2014

(65) Prior Publication Data

US 2015/0067952 A1 Mar. 12, 2015

Related U.S. Application Data

(60) Provisional application No. 61/907,532, filed on Nov. 22, 2013.

(51) Int. Cl.
*B65H 75/14* (2006.01)
*B65H 18/00* (2006.01)
(Continued)

(52) U.S. Cl.
CPC ............. *B65H 75/14* (2013.01); *A42B 3/26* (2013.01); *A61F 9/025* (2013.01); *B65H 16/06* (2013.01);
(Continued)

(58) Field of Classification Search
CPC ......... A42B 3/04; A42B 3/0406; A42B 3/042; A42B 3/185; A42B 3/30; A42B 3/18;
(Continued)

(56) References Cited

U.S. PATENT DOCUMENTS

| | | | |
|---|---|---|---|
| 1,969,710 A * | 8/1934 | Jones | A61F 9/025 2/438 |
| 1,994,103 A * | 3/1935 | Huey | A61F 9/025 2/8.2 |

(Continued)

FOREIGN PATENT DOCUMENTS

WO 2009120059 A2 10/2009

*Primary Examiner* — Khoa Huynh
*Assistant Examiner* — Jocelyn Wu
(74) *Attorney, Agent, or Firm* — Gerald R Prettyman

(57) ABSTRACT

Disclosed is an Off-Road Rolling Film Vision System comprising a Controller Module (200), a Takeup Module (300), and a Rollout Module (400). The Controller Module (200) comprises a Command Input (205), a Controller Process Module (210), a Command Transmitter (215), and a Power Supply (220). The Controller Module (200) is configured to remotely control a Motor (325) in the Takeup Module (300). The Command Input (205) comprises at least one Button configured to accept a knuckle bump for controlling a Motor (325) in the Takeup Module (300) when the Controller Module (200) is attached to a handlebar of an off-road vehicle. The at least one Button configured to accept a knuckle bump may be configured to be adjacent to a user's metacarpophalangeal index finger joint. The at least one Button configured to accept a knuckle bump may be configured to be adjacent to a user's metacarpophalangeal thumb joint. The Takeup Module (300) comprises a Motor Compartment (305), a Takeup Spool Compartment (310), a Takeup Spool Gear Compartment (315), a Takeup Film Window (320), a Motor (325), a Motor Gearbox (330), and at least one Takeup Spool Gear (340). The Takeup Module (300) may further comprise a Takeup Spool Window (350) configured to provide a view of a Takeup Spool (345) within the Takeup Module (300). Also disclosed is a Takeup Spool (500) comprising a Spool Alignment Tab Wheel (505), a Spool Ribbed Shaft (510), a Rib Quarter Section Cutout (515), a Spool Alignment Slot Wheel (525), a Spool Alignment Tab (530), a Spool Alignment Slot (535), a Plurality of Wheel Cutouts (540), and a Plurality of Wheel Slots (545). Also disclosed is a method for maintaining clear vision with goggles comprising receiving a command input via a knuckle bump, transmitting a designated signal to a module comprising a Motor and a Takeup Spool, activating the Motor to cause the Takeup Spool to rotate, and winding a Transparent Film a designated distance over goggles.

21 Claims, 17 Drawing Sheets

(51) Int. Cl.
*A61F 9/02* (2006.01)
*B65H 18/10* (2006.01)
*A42B 3/26* (2006.01)
*B65H 16/06* (2006.01)
*B65H 18/02* (2006.01)

(52) U.S. Cl.
CPC ........... *B65H 18/00* (2013.01); *B65H 18/028* (2013.01); *B65H 18/103* (2013.01); *B65H 2301/4493* (2013.01); *B65H 2557/11* (2013.01)

(58) Field of Classification Search
CPC . A42B 3/24; A61F 9/025; A61F 9/029; B65H 75/14; B65H 16/06; B65H 18/028; B65H 18/103; B65H 18/00; B65H 2701/19; B65H 2557/11; B65H 2301/4493
USPC ..................................................... 2/438, 422
See application file for complete search history.

(56) References Cited

U.S. PATENT DOCUMENTS

| | | | |
|---|---|---|---|
| 2,259,680 A * | 10/1941 | Caudell | A62B 18/04 128/201.14 |
| 2,485,117 A * | 10/1949 | Settle | A62B 18/003 2/8.1 |
| 2,902,332 A | 9/1959 | Bauer | |
| 3,439,596 A | 4/1969 | Peterson et al. | |
| 3,595,148 A | 7/1971 | Cagen | |
| 3,722,385 A | 3/1973 | Kamp et al. | |
| 3,946,442 A * | 3/1976 | Wallander | A42B 3/26 2/9 |
| 4,428,081 A * | 1/1984 | Smith | A61F 9/025 2/422 |
| 4,528,701 A * | 7/1985 | Smith | A61F 9/02 2/438 |
| 4,748,697 A | 6/1988 | Hodnett | |
| 5,203,035 A * | 4/1993 | Lawlor | A62B 18/082 2/434 |
| 5,412,446 A | 5/1995 | Rydelek | |
| 5,993,080 A | 11/1999 | Clough | |
| 6,047,412 A * | 4/2000 | Wilson, II | A61F 9/025 2/422 |
| 6,073,296 A * | 6/2000 | Bouguerfa | A42B 3/26 15/102 |
| 6,415,452 B1 * | 7/2002 | Watanabe | A61F 9/025 2/438 |
| 6,416,177 B1 * | 7/2002 | Gibson | A61F 9/02 2/438 |
| 6,976,627 B1 | 12/2005 | Culp et al. | |
| 8,261,375 B1 * | 9/2012 | Reaux | A41D 13/1184 128/201.15 |
| 2002/0176710 A1 | 11/2002 | Saito et al. | |
| 2005/0219462 A1 | 10/2005 | Breish et al. | |
| 2012/0023647 A1 * | 2/2012 | Park | A61F 9/025 2/438 |
| 2014/0008593 A1 | 1/2014 | Kingerly | |

\* cited by examiner

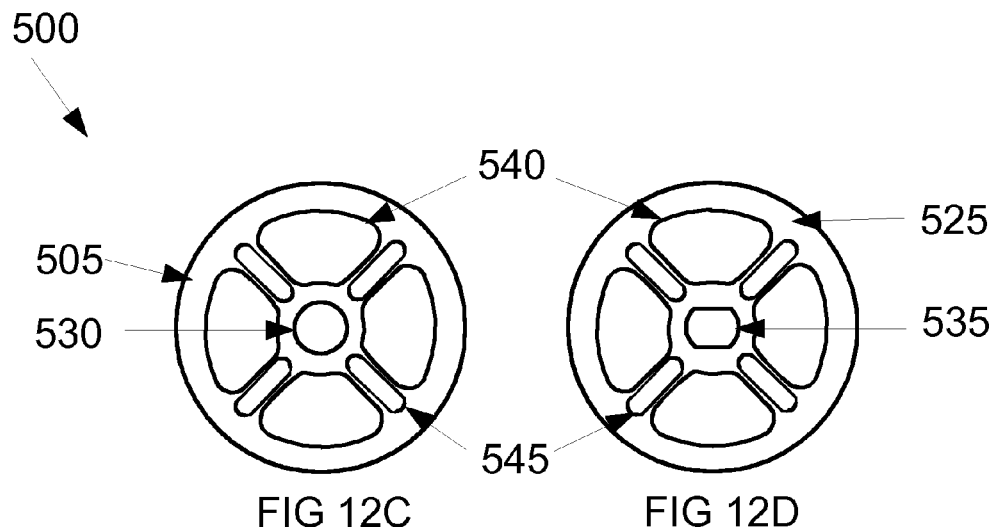
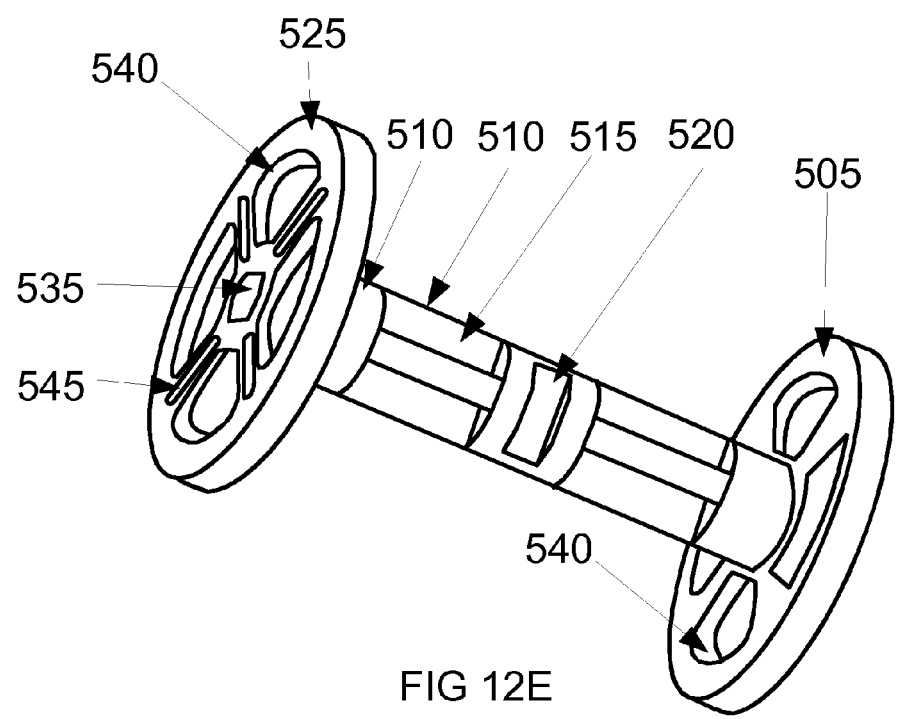

OFF-ROAD ROLLING FILM VISION SYSTEM

CROSS-REFERENCE TO RELATED APPLICATION

This application claims the benefit of priority of U.S. Provisional Patent Application 61/907,532 filed Nov. 22, 2013 and titled "AUTO ROLLING FILM SYSTEM," the disclosure of which is incorporated by reference. This application is related to four design patent applications filed the same date and by the same inventor and titled "SPOOL FOR OFF-ROAD ROLLING FILM VISION SYSTEM", "TAKEUP MODULE for OFF-ROAD ROLLING FILM VISION SYSTEM", "ROLLOUT MODULE FOR OFF-ROAD ROLLING FILM VISION SYSTEM" and "CONTROLLER FOR OFF-ROAD ROLLING FILM VISION SYSTEM."

STATEMENT REGARDING FEDERALLY SPONSORED RESEARCH OR DEVELOPMENT

Not Applicable

BACKGROUND OF THE INVENTION

Field of Invention

The invention relates generally to the field of protective hardware for off-road riding and racing and other off-road and more specifically to devices aiding riders' ability to see.

Description of Related Art

Off-road racing and riding provides entertainment and thrills to both participants and spectators. During the run, the vehicles cast up dirt and mud. Goggles and glasses can be covered by this dirt and mud, obscuring participants' vision.

SUMMARY OF THE INVENTION

Embodiments are directed to an OFF-ROAD ROLLING FILM VISION SYSTEM (100) for giving off-road riders a hands-free method of keeping their goggles or face shield clear of dust, mud and other debris by having a transparent film moving across the goggles or face shield to collect and remove the dust, mud and other debris.

In a preferred embodiment, the OFF-ROAD ROLLING FILM VISION SYSTEM (100) comprises a Controller Module (200), a Takeup Module (300), and a Rollout Module (400).

In some embodiments, the Controller Module (200) comprises a Command Input (205), a Controller Process Module (210), a Command Transmitter (215), and a Power Supply (220).

In some embodiments, the Command Input (205) comprises at least one Button configured to accept a knuckle bump for controlling a Motor (325) moving a Transparent Film (105) across goggles.

In some embodiments, the at least one Button configured to accept a knuckle bump is configured to be adjacent to a user's metacarpophalangeal index finger joint.

In some embodiments, the at least one Button configured to accept a knuckle bump is configured to be adjacent to a user's metacarpophalangeal thumb joint.

In some embodiments, the Power Supply (220) comprises a battery.

In some embodiments, the Takeup Module (300) comprises a Takeup Spool Window (350) configured to provide a view of a Transparent Film (105) on a Takeup Spool (345) within the Takeup Module (300).

In some embodiments, the Rollout Module (400) comprises a Rollout Spool Window (450) configured to provide a view of a Rollout Spool (445) within the Rollout Module (400).

In some embodiments, a Spool (500) comprises a Spool Alignment Tab Wheel (505), a Spool Ribbed Shaft (510), a Rib Quarter Section Cutout (515), a Spool Alignment Slot Wheel (525), a Spool Alignment Tab (530), a Spool Alignment Slot (535), a Plurality of Wheel Cutouts (540), and a Plurality of Wheel Slots (545).

In some embodiments, the Rollout Spool Tensioner (440) comprises a Rollout Spool Tensioner Spool Countersink (441) and a Rollout Spool Tensioner Spool Latch (442) capable of engaging a Rollout Spool (445) for applying tension to the Rollout Spool (445).

The OFF-ROAD ROLLING FILM VISION SYSTEM (100) may be used with a motorcycle, an All-Terrain Vehicle, a snowmobile, an automobile (as with open vehicle driving or races) or any other situation where a driver or rider prefers to have clear vision.

BRIEF DESCRIPTION OF THE DRAWINGS

FIGS. 12A, 12B, 12C, 12D and 12E show embodiments of a Spool (500).

DETAILED DESCRIPTION OF THE INVENTION

Figure 1:
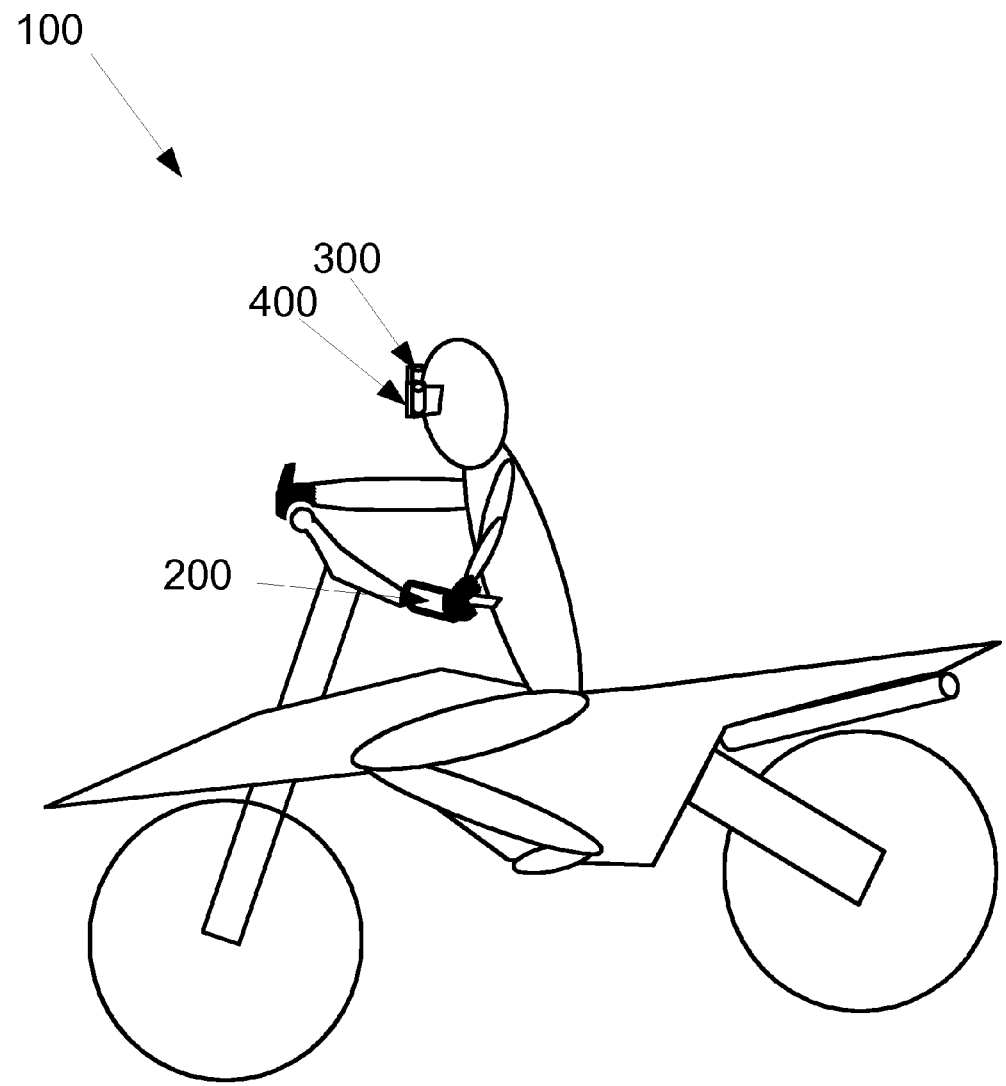
FIG. 1 shows an exemplary OFF-ROAD ROLLING FILM VISION SYSTEM (100) for giving off-road racers and other off-road fans a hands-free method of keeping their goggles or face shield clear of dust, mud and other debris by having a transparent film moving across the goggles or face shield to collect and remove the dust, mud and other debris.

FIG. 1 shows an exemplary OFF-ROAD ROLLING FILM VISION SYSTEM (100) for giving off-road racers and other off-road fans a hands-free method of keeping their goggles or face shield clear of dust, mud and other debris by having a transparent film moving across the goggles or face shield to collect and remove the dust, mud and other debris. The exemplary OFF-ROAD ROLLING FILM VISION SYSTEM (100) comprises a Controller Module (200), a Takeup Module (300), and a Rollout Module (400). Details of the exemplary OFF-ROAD ROLLING FILM VISION SYSTEM (100) with a preferred and optional embodiments are subsequently described.

Figure 2A:
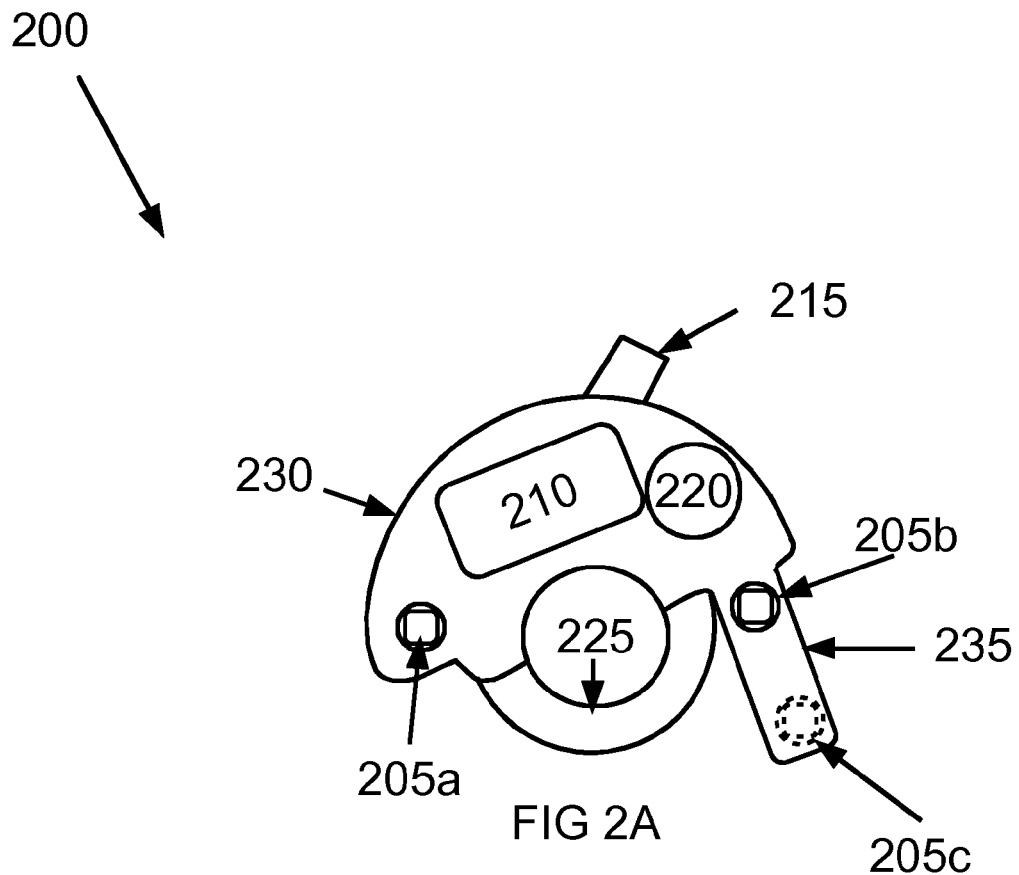
FIGS. 2A and 2B show an embodiment of the Controller Module (200).
Figure 2B:
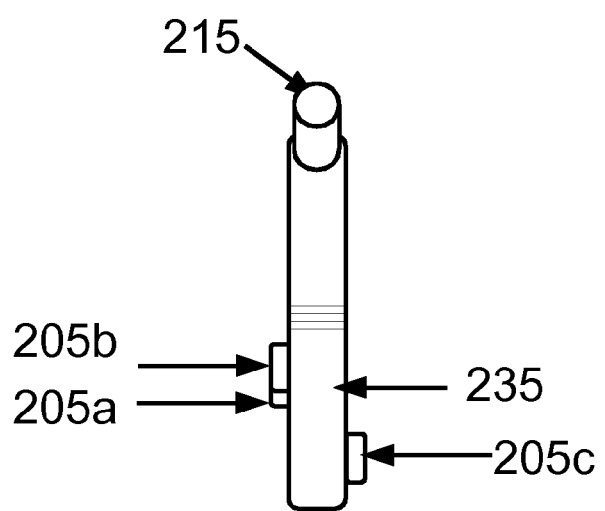

FIGS. 2A and 2B shows an embodiment of the Controller Module (200). The Controller Module (200) embodiment shown comprises a Command Input (205), a Controller Process Module (210), a Command Transmitter (215), a Power Supply (220), a Vehicle Attachment (225), a Housing (230) and a Controller Extension (235). Some embodiments comprise a Clothing Attachment (not shown) rather than a Vehicle Attachment (225).

The Command Input (205) may be any device capable of receiving a designated signal from a user to engage a designated communication between the Controller Module (200) and at least one of the Takeup Module (300) and the Rollout Module (400). The designated signal would execute a signal to at least one of the Takeup Module (300) and the Rollout Module (400) to roll-out, or roll-in film from the Takeup Module (300) to the Rollout Module (400).

In some embodiments, the Command Input (205) may be at least one mechanical switch. In some embodiments, the Command Input (205) may be at least one electronic switch. The Command Input (205) may be a toggle switch. In some embodiments, the Command Input (205) may be tiered switch comprising a plurality of settings so that a user may set the Command Input (205) to one of the plurality of run settings, including for continuous run, timed run, intermittent run, stop, or manual advancing of the Transparent Film (105).

In a preferred embodiment, there are three Buttons for the Command Input (205). For example, for instances of installation of the OFF-ROAD ROLLING FILM VISION SYSTEM (100) on a motorized vehicle with a handlebar, there may be a first Command Input Button (205a) positioned on the Controller Module (200) to be adjacent to a user's index finger first knuckle (the metacarpophalangeal joint). A second Command Input Button (205b) might be positioned on the Controller Module (200) to be adjacent to a user's thumb metacarpophalangeal knuckle. A third Command Input Button (205c) might be positioned on a Controller Extension (235) of the Controller Module (200) such that a user might touch the button by moving the user's thumb around the Controller Extension (235).

The Controller Process Module (210) receives and transmits signals for the Controller Module (200). In a preferred embodiment, Controller Process Module (210) receives a signal from the Command Input (205), transmits a "RUN" signal via the Command Transmitter (215) to at least one of the Takeup Module (300) and the Rollout Module (400), and then, to avoid an accidental extraneous run of the Transparent Film (105) Controller Process Module (210) invokes a delay to ignore extraneous signals for a designated time. In a typical embodiment, the "RUN" signal advances the Transparent Film (105) about six or seven inches, then delays for two to six seconds.

In some embodiments, Controller Process Module (210) receives one or more signals from the Command Input (205), and then transmits the correct corresponding signal via the Command Transmitter (215) to at least one of the Takeup Module (300) and the Rollout Module (400). A "START" command may cause the Transparent Film (105) to advance the Transparent Film (105) until a "STOP" signal is sent. An "INTERMITTENT" command may cause the Transparent Film (105) to advance the Transparent Film (105) in fixed increments of length or time.

A Command Transmitter (215) transmits the designated signal from the Controller Module (200) to at least one of the Takeup Module (300) or the Rollout Module (400). In some embodiments, the Command Transmitter (215) uses a wireless communication system, which may be infra-red (IR) technology, radio (RC, remote controlled) technology, wireless communications for exchanging data over short distances using short-wavelength ultrahigh frequency radio waves from 2.4 to 2.485 GHz and capable of connecting up to seven devices, i.e., Bluetooth technology, wireless communications for exchanging small data packets over short distances at up to 100 kilobits per second using a source-routed mesh network architecture i.e. Z-Wave technology, wireless communications for exchanging data over short distances following the IEEE 802.15.4 standard and using low-power low-bandwidth line-of-sight transmissions at up to 250 kbits per second, i.e., Zigbee technology, or other wireless connector system, though some embodiments may have a wired communication system to at least one of the Takeup Module (300) or the Rollout Module (400).

A Power Supply (220) powers the Controller Process Module (210), the Command Input (205) and the Command Transmitter (215). In some embodiments, the Power Supply (220) is a button battery.

A Vehicle Attachment (225) secures the Controller Module (200) and its components to the handlebars or other convenient location on the vehicle or the person. The Vehicle Attachment (225) may be made any material or composite, including a metal, a plastic, wood, ceramic, etc.

A Housing (230) provides attachment of the components of the Controller Module (200) relative to each other, as well as for environmental protection. The Housing (230) may be made of any material or composite, including a metal, a plastic, wood, ceramic, etc. In some embodiments, the Housing (230) is made of metal, which may be studier and easier to fabricate. In some embodiments, the Housing (230) is made of plastic, including but not limited to ABS, PVC, or other thermoplastic materials, a plastic-composite or other organic materials which tends to be lighter-weight than a similarly fashioned Housing (230) made of metal.

Some embodiments may comprise a Controller Extension (235) to extend the Controller Module (200) sufficient below the handlebars of the off-road vehicle for a person to use the thumb to engage one of the Buttons (205 a, b or c) of the Command Inputs.

Figure 2C:
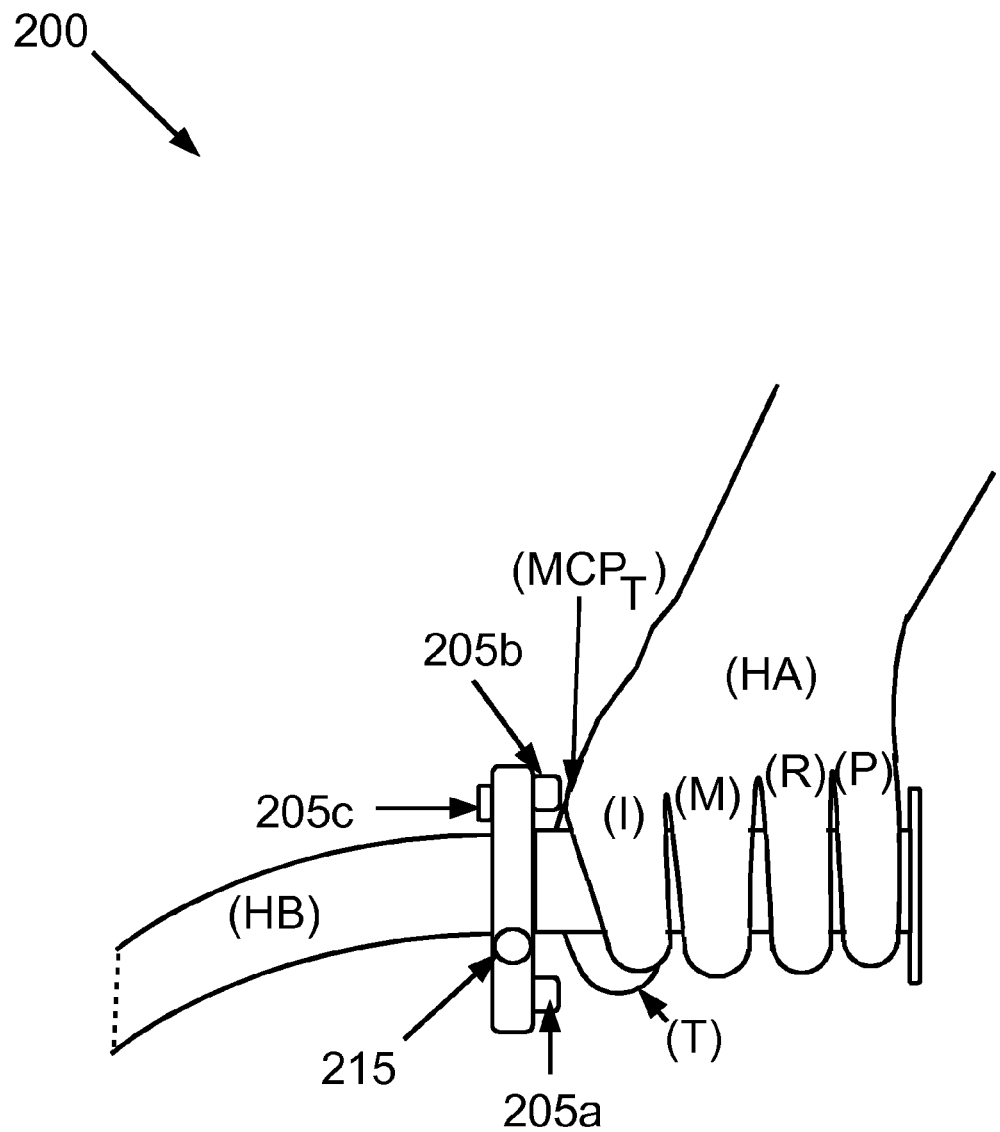
FIGS. 2C and 2D show the Controller Module (200) in use.
Figure 2D:
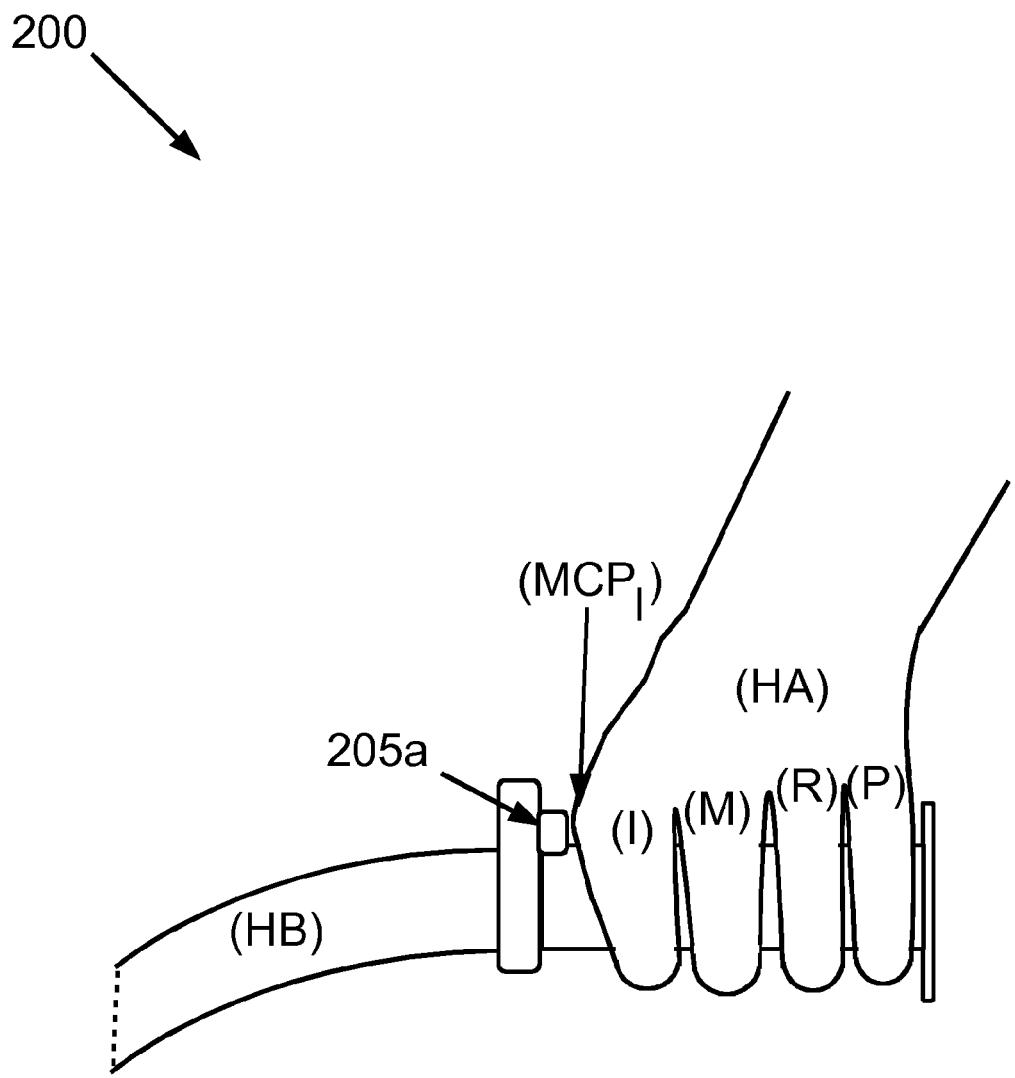

FIGS. 2C and 2D show the Controller Module (200) in use on a handlebar with a sitting and a standing user, respectively. In a preferred embodiment, the Controller Module (200) is on the left side of the handlebar as the vehicle throttle is typically on the right side of the handlebar.

Shown in FIG. 2C from a somewhat top view looking at a user sitting on a vehicle with handlebars (HB) are the Controller Module (200), a first Command Input Button (205a), a second Command Input Button (205b), a third Command Input Button (205c), the Command Transmitter (215) and a Hand (HA) with an index finger (I), a middle finger (M), a ring finger (R), a pinky finger (P), and a Thumb (T) with a metacarpophalangeal thumb joint ($MCP_T$).

When a user is sitting on an off-road vehicle with a handlebar (HB), the user's metacarpophalangeal thumb joint ($MCP_T$) will typically be near the second Command Input Button (205b). In this position, a user may use a knuckle bump of the metacarpophalangeal thumb joint ($MCP_T$) to send a command to the Takeup Module (300) to RUN the Transparent Film (105) a specified length or time. A user thus does not have to remove his or her hand from the handlebar to actuate the OFF-ROAD ROLLING FILM VISION SYSTEM (100).

Shown in FIG. 2D from a somewhat front position looking at a user standing on a vehicle with handlebars are the Controller Module (200), the first Command Input Button (205a), the Command Transmitter (215) with a Hand (HA), with an index finger (I), a middle finger (M), a ring finger (R), a pinky finger (P), and a metacarpophalangeal index finger joint ($MCP_I$). In this position, a user's thumb is behind the handlebars (HB), while the second and third are typically also out of view behind the handlebars (HB).

When a user is standing on an off-road vehicle with a handlebar, the user's metacarpophalangeal index finger joint ($MCP_I$) will typically be near the first Command Input Button (205a). In this position, a user may use a knuckle bump of the metacarpophalangeal thumb joint ($MCP_T$) to send a command to the Takeup Module (300) to RUN the Transparent Film (105) a specified length or time. A user thus does not have to remove his or her hand from the handlebar to actuate the OFF-ROAD ROLLING FILM VISION SYSTEM (100).

Figure 3:
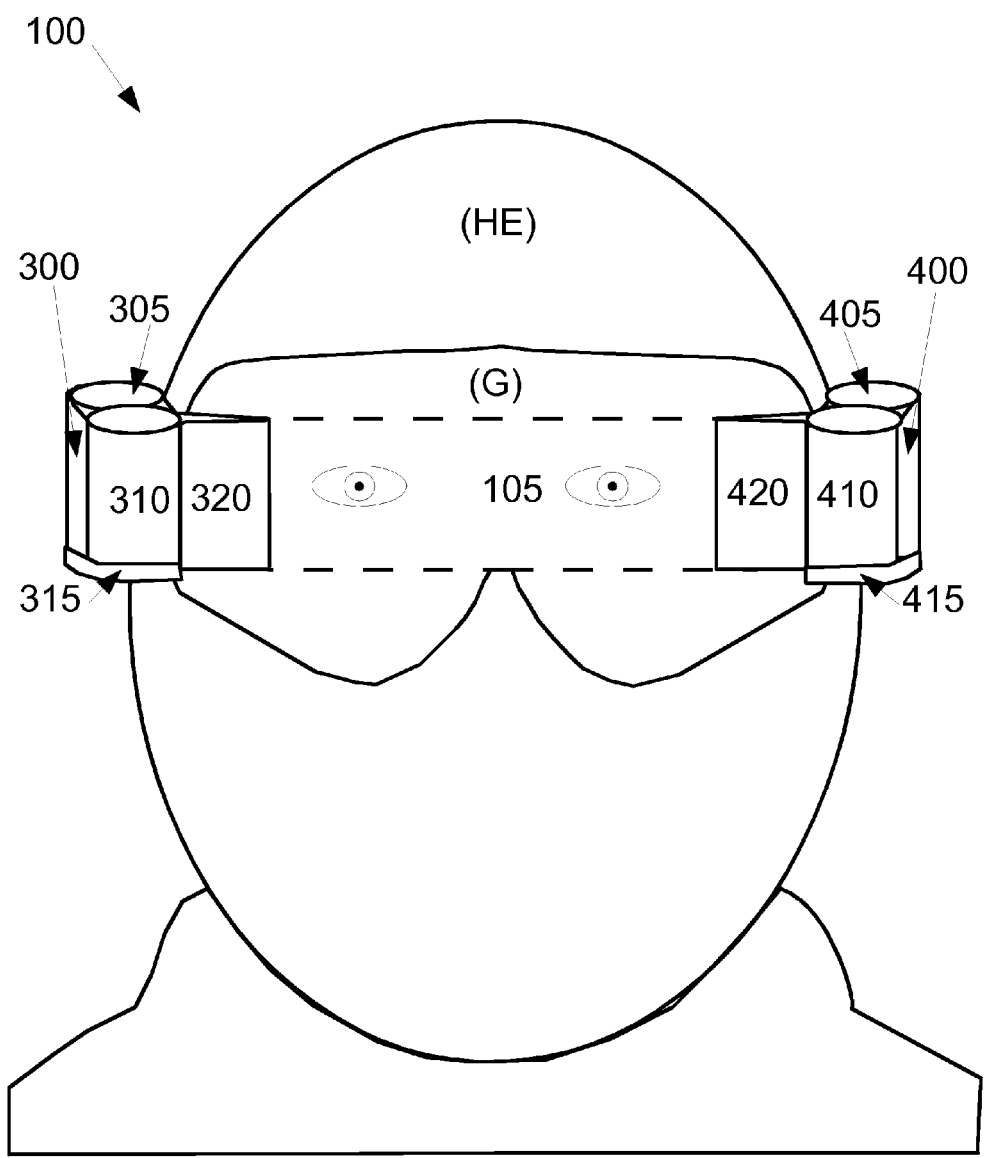
FIG. 3 shows embodiments of the Takeup Module (300) and the Rollout Module (400) as typically placed on a user's helmet.

FIG. 3 shows embodiments of the Takeup Module (300) and the Rollout Module (400) as the OFF-ROAD ROLLING FILM VISION SYSTEM (100) might be used.

Shown in FIG. 3 are a Takeup Module (300), and a Rollout Module (400) positioned on a Helmet (HE) such that a Transparent Film (105) is in front of a user, or on goggles (G) or other eyewear.

The Takeup Module (300) is capable of receiving and holding a Transparent Film (105) as dispensed through the OFF-ROAD ROLLING FILM VISION SYSTEM (100), and contains various components for receiving and holding the film through the OFF-ROAD ROLLING FILM VISION SYSTEM (100).

In a preferred embodiment, the Takeup Module (300) comprises a Motor Compartment (305), a Takeup Spool Compartment (310), a Takeup Spool Gear Compartment (315), and a Takeup Film Window (320).

The Motor Compartment (305) holds and protects a motor which functions to transport the Transparent Film (105) between the Rollout Module (400) and the Takeup Module (300). Details of the Motor Compartment (305) will subsequently be shown and described.

The Takeup Spool Compartment (310) holds and protects the Transparent Film (105) as dispensed through the OFF-ROAD ROLLING FILM VISION SYSTEM (100). Details of the Takeup Spool Compartment (310) will subsequently be shown and described.

The Takeup Spool Gear Compartment (315) comprises a gear space and at least one gear for driving a Takeup Spool (345) (not shown here) which functions to takeup the Transparent Film (105). The one or more components of the Takeup Spool Gear Compartment (315) also provide proper tension to the Transparent Film (105) as it travels through the OFF-ROAD ROLLING FILM VISION SYSTEM (100). Details of the Takeup Spool Gear Compartment (315) will subsequently be shown and described.

The Takeup Film Window (320) provides multiple functions to the OFF-ROAD ROLLING FILM VISION SYSTEM (100). It provides a distance between the open air and the moving parts in the interior of the Takeup Module (300), thereby protecting them from the elements. In addition, the Takeup Film Window (320) serves as a steady travel path for the Transparent Film (105). In addition, when transparent, the Takeup Film Window (320) provides a user a view of and through the Transparent Film (105) as it enters the Takeup Module (300). Other details of the Takeup Film Window (320) will subsequently be shown and described.

The Takeup Module (300) and its components made be constructed of any material suitable for fulfilling the functions presented. In some embodiments, the Takeup Module (300) and its components made be constructed of plastic. In some embodiments, the Takeup Module (300) and its components made be constructed of ABS, PVC, or other thermoplastic materials, a plastic-composite or other organic materials.

In some embodiments, the Takeup Module (300) and its components made be constructed of metal. In some embodiments, the Takeup Module (300) and its components made be constructed of wood or a wood-composite.

The Rollout Module (400) is capable of receiving and storing the Transparent Film (105) as it is dispensed through the OFF-ROAD ROLLING FILM VISION SYSTEM (100), and contains various components for receiving and storing the Transparent Film (105) through the OFF-ROAD ROLLING FILM VISION SYSTEM (100).

In a preferred embodiment, the Rollout Module (400) comprises a Battery Compartment (405), a Rollout Spool Compartment (410), a Rollout Spool Gear Compartment (415), and a Rollout Film Window (420).

The Battery Compartment (405) is configured to hold and draw power from a Battery (425) for powering the OFF-ROAD ROLLING FILM VISION SYSTEM (100). Details of the Battery Compartment (405) will subsequently be shown and described.

The Rollout Spool Compartment (410) holds and stores the dispensed Transparent Film (105) as it has been passed through the OFF-ROAD ROLLING FILM VISION SYSTEM (100). Details of the Rollout Spool Compartment (410) will subsequently be shown and described.

The Rollout Spool Gear Compartment (415) comprises a space for at least one Rollout Spool Tensioner (440) (not shown here) for rolling out the Transparent Film (105) from the Rollout Module (400) to the Takeup Module (300).

The Rollout Film Window (420) provides multiple functions to the OFF-ROAD ROLLING FILM VISION SYSTEM (100). It provides a distance between the open air and the moving parts in the interior of the Rollout Module (400), thereby protecting them from the elements. In addition, Rollout Film Window (420) serves as a steady travel path for the Transparent Film (105). In addition, the Rollout Film Window (420) provides a user a view of and through the Transparent Film (105) as it exits the Rollout Module (400). Other details of the Rollout Film Window (420) will subsequently be shown and described.

Ideally, the Takeup Module (300) and the Rollout Module (400) would weigh about the same to provide balance for user comfort when affixed to Goggles ("G"). In a preferred embodiment, the OFF-ROAD ROLLING FILM VISION SYSTEM (100) is affixed with fasteners (not shown) to the Goggles ("G") using the Takeup Goggle Pad (360) and Rollout Goggle Pad (460), respectively, which are subsequently shown and described.

Figure 4:
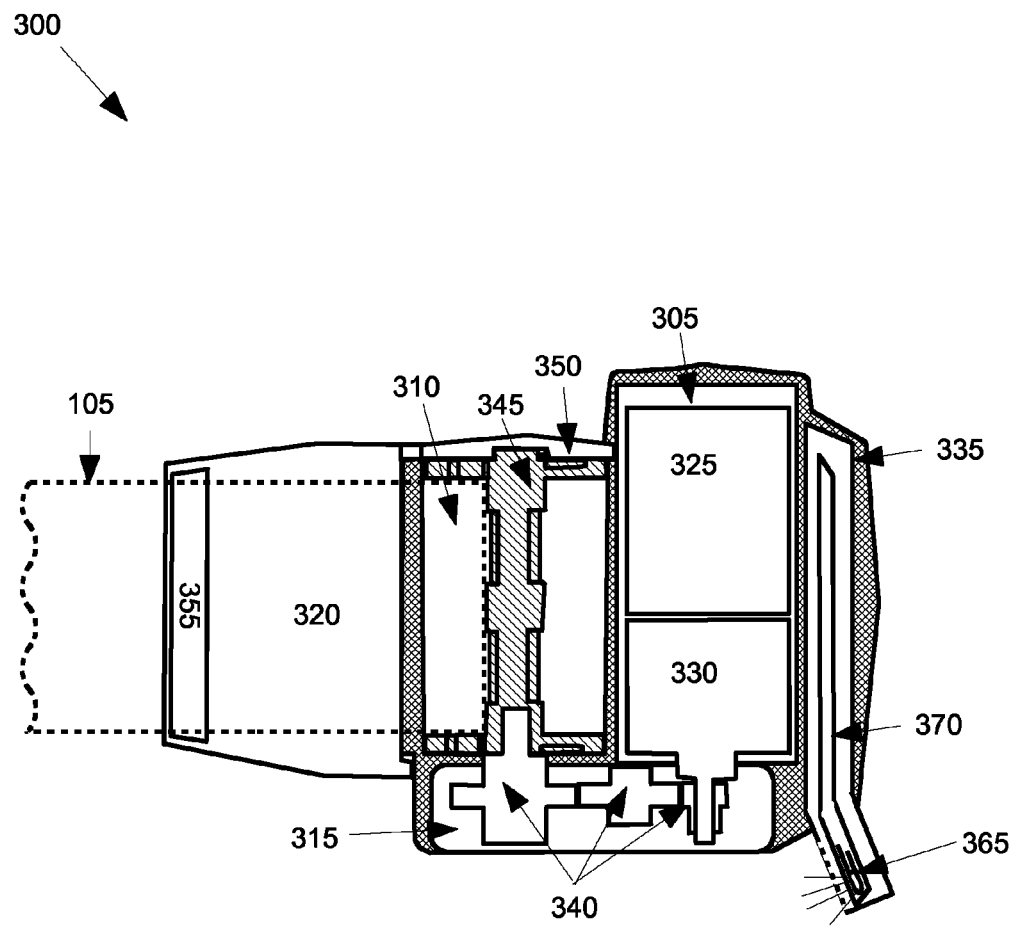
FIG. 4 shows an internal view of a embodiment of the Takeup Module (300).

FIG. 4 shows an internal view of a embodiment of the Takeup Module (300). Shown in FIG. 4 are the Takeup Module (300), the Transparent Film (105) placed as it may be aligned for use in the Takeup Module (300), a Motor Compartment (305), a Takeup Spool Compartment (310), a Takeup Spool Gear Compartment (315), a Takeup Film Window (320), a Motor (325), a Motor Gearbox (330), a Takeup Circuit Board Compartment (335), an at least one Takeup Spool Gear (340), a Takeup Spool (345), a Takeup Spool Window (350), a Takeup Film Pad (355), a Takeup Receiver (365) and a Takeup Circuit Board (370).

The Motor Compartment (305) secures and protects a Motor (325), which receives power from a Power Supply (which is subsequently shown and described), and converts and transmits power to drive a Takeup Spool (345).

Coupled to the Motor (325) is a Motor Gearbox (330), which functions to convert the native speed and torque of the Motor (325) to a proper speed and torque for the Takeup Spool (345) to takeup the Transparent Film (105).

Some embodiments may comprise at least one Takeup Spool Gear (340) coupled to the Motor Gearbox (330) within the Takeup Spool Gear Compartment (315). When present, the at least one Takeup Spool Gear (340) transmits the output power speed and torque from the Motor Gearbox (330) to the Takeup Spool (345). The Motor (325), a Motor Gearbox (330), and at least one Takeup Spool Gear (340) are configured to rotate a Takeup Spool (345) within the Takeup Module (300). In some embodiments, the at least one Takeup Spool Gear (340) may comprise a plurality of gears, which may convert the output power speed and torque from the Motor Gearbox (330) to a different power speed and torque for transmission to the Takeup Spool (345).

The at least one Takeup Spool Gear (340) may be constructed of any material suitable for receiving and transmitting power between the Motor Gearbox (330) and the Takeup Spool (345). In some embodiments, the at least one Takeup Spool Gear (340) may be made of plastic, some of which are elsewhere described herein. In some embodiments, the at least one Takeup Spool Gear (340) may be made of metal.

The term, at least one Takeup Spool Gear (340), is not intended to limit the at least one Takeup Spool Gear (340) actually to gears. In some embodiments, the at least one Takeup Spool Gear (340) may comprise a drive belt. As the function of the at least one Takeup Spool Gear (340) is to transmit the output power speed and torque from the Motor Gearbox (330) to the Takeup Spool (345), the at least one Takeup Spool Gear (340) may comprise any energy transmission type suitable for the function.

Overall, the Motor (325), Motor Gearbox (330) and Takeup Spool Gear (340) (if present) provide a proper balance of tension and takeup (measured linearly) so the Transparent Film (105) moves at the proper rate for the environmental conditions, and without free run, bunching, tears or rips.

Within the Takeup Spool Compartment (310) is a Takeup Spool (345). The Takeup Spool (345) receives and stores the transparent film coming into the Takeup Module (300). Details about the Takeup Spool (345) will subsequently be shown and described.

In some embodiments, a Takeup Spool Window (350) is attached to the Takeup Module (300) atop the Takeup Spool Compartment (310) to provide a view of the Takeup Spool (345). This view of the Takeup Spool (345) grants a visible indication of how much Transparent Film (105) is present on the Takeup Spool (345). In some embodiments, the Takeup Spool Window (350) is made of transparent plastic. In some embodiments, the Takeup Spool Window (350) is made of glass. In some embodiments, the Takeup Spool Window (350) is made of a non-transparent material interspersed with a transparent material.

As shown in FIG. 4, in some embodiments, a Takeup Film Pad (355) is present to remove debris from the transparent film as the Transparent Film (105) enters the Takeup Module (300). The Takeup Film Pad (355) may act as knife to scrap debris from the Transparent Film (105), or as a blotter to absorb debris from the Transparent Film (105), or both. The Takeup Film Pad (355) may be any material suitable, including soft materials such as paper, natural organic materials such as rubber, artificial organic materials such as foam, plasticized PVC, or harder materials including rigid plastics, wood, or metal.

The Takeup Receiver (365) receives command signals from the Controller Module (200) via the Command Transmitter (215). As with the Command Transmitter (215), Takeup Receiver (365) may use a wireless connector system, which may be infra-red (IR), radio (RC— remote controlled), wireless communications for exchanging data over short distances using short-wavelength ultrahigh frequency radio waves from 2.4 to 2.485 GHz and capable of connecting up to seven devices, i.e., Bluetooth technology, wireless communications for exchanging small data packets over short distances at up to 100 kilobits per second using a source-routed mesh network architecture i.e., Z-Wave technology, wireless communications for exchanging data over short distances following the IEEE 802.15.4 standard and using low-power low-bandwidth line-of-sight transmissions at up to 250 kbits per second, i.e., Zigbee, or other wireless connector system, though in some embodiments, the Controller Module (200) may be wire-connected to the Takeup Receiver (365).

The Takeup Circuit Board (370) receives the command signals from the Takeup Receiver (365) and drives the Motor (325) as described herein, according to the command signals received.

Figure 5:
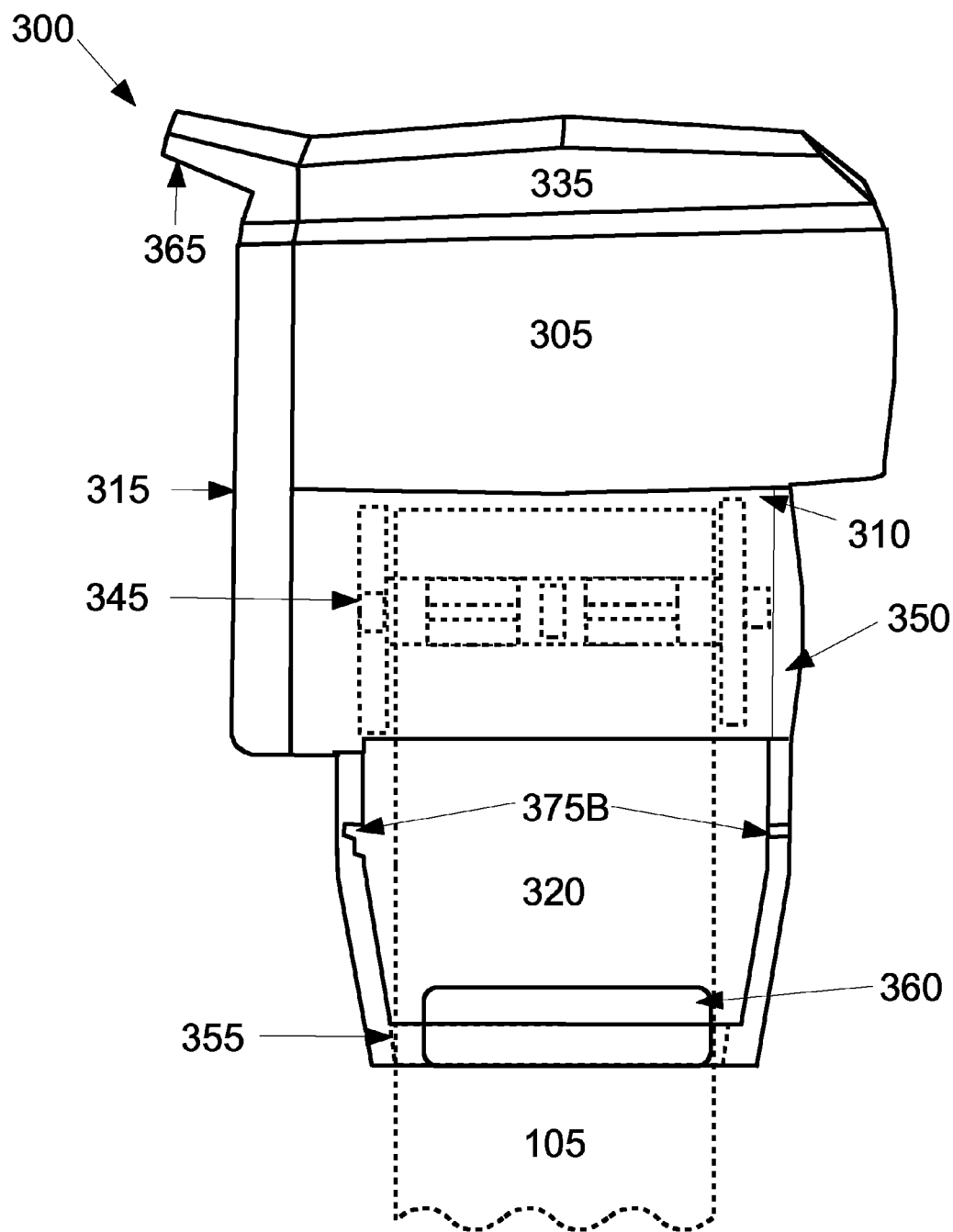
FIG. 5 shows an back view of a embodiment of the Takeup Module (300).

FIG. 5 shows a back view of a embodiment of the Takeup Module (300). Shown in FIG. 5 are the Takeup Module (300), the Transparent Film (105) placed as it may be aligned for use in the Takeup Module (300), the Motor Compartment (305), the Takeup Spool Compartment (310), the Takeup Spool Gear Compartment (315), the Takeup Film Window (320), the Takeup Circuit Board Compartment (335), a Takeup Spool (345) within the Takeup Spool Compartment (310), the Takeup Spool Window (350), a Takeup Film Pad (355), a Takeup Goggle Pad (360), a Takeup Receiver (365) and a Takeup Spool Window Hinge-Connector (375B).

The back view of a embodiment of the Takeup Module (300) differs primarily from the internal view in showing the Takeup Goggle Pad (360) and the Takeup Spool Window Hinge-Connector (375B).

The primary function of the Takeup Goggle Pad (360) is to provide a stability point of the Takeup Module (300) against a user's helmet. The Takeup Goggle Pad (360) may be affixed to the Goggles (see FIG. 3) to mitigate movement and absorb activity vibration, which aids maintaining the Takeup Module (300) in place, which in turn keeps the transparent film in proper place for the user to use the OFF-ROAD ROLLING FILM VISION SYSTEM (100), and mitigates the Takeup Module (300) from scratching the goggles. The Takeup Goggle Pad (360) may be affixed to the goggles (G) with any suitable affixing technique, including screws or bolts, or an adhesive.

The Takeup Spool Window Hinge-Connector (375B) aids in proper placement of the transparent film by allowing the user to move the Takeup Film Window (320) to align the Transparent Film (105) within it. In a preferred embodiment, there are two parts of the Takeup Spool Window Hinge-Connector (375A and 375B); 375A is omitted from FIG. 5 for clarity of other structure. In some embodiments, the Takeup Spool Window Hinge-Connector (375A and 375B)

are pins and slots. In some embodiments, the Takeup Spool Window Hinge-Connector (375A and 375B) are a hinge and a pin.

Figure 6:
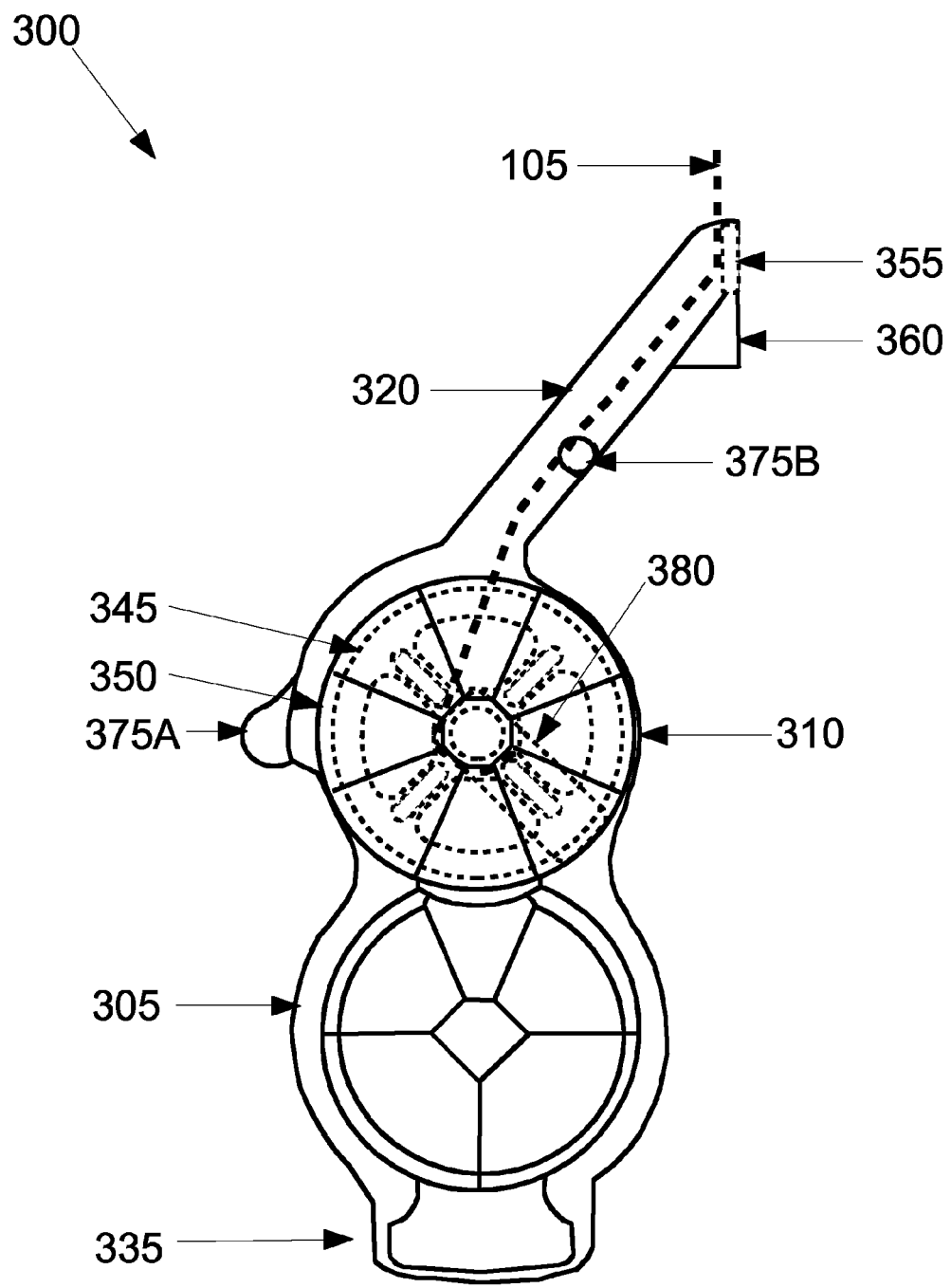
FIG. 6 shows a top view of an embodiment of the Takeup Module (300).

FIG. 6 shows a top view of an embodiment of the Takeup Module (300).

Shown in FIG. 6 are the Takeup Module (300), the Transparent Film (105) placed as it may be aligned for use in the Takeup Module (300), a Motor Compartment (305), a Takeup Spool Compartment (310), a Takeup Film Window (320), a Takeup Circuit Board Compartment (335), a Takeup Spool (345) as viewed through a Takeup Spool Window (350), a Takeup Film Pad (355), a Takeup Goggle Pad (360), a Takeup Spool Window Hinge-Connector (375A and 375B) and a Spool Tab Slot (380).

As shown in FIG. 6, the Takeup Spool Window (350) rests above the Takeup Spool (345) so that a person may see how much Transparent Film (105) is present on the Takeup Spool (345). Though shown as wholly transparent in entirety, the Takeup Spool Window (350) may be partially transparent, or may be opaque in part and transparent in part, (as by a diametrical slot), or may be wholly opaque, for instances when other techniques might be used to determine remaining spool capacity.

Also shown in FIG. 6 is a Spool Tab Slot (380) on the Takeup Spool Window (350) within the Takeup Spool Compartment (310). The Spool Tab Slot (380) provides passage for the Spool Alignment Tab (530), (see FIG. 12A, etc.) during loading of the Takeup Spool (345) into the Takeup Module (300) and a way to secure the Takeup Spool (345) within the Takeup Spool Compartment (310).

FIG. 6 also presents a view of the Transparent Film (105) and the Takeup Film Pad (355) within the Takeup Spool Window (350) as the Transparent Film (105) might be aligned within the Takeup Film Pad (355) and wrapped around the Takeup Spool (345). The particular alignment of the Takeup Film Pad (355) within the Takeup Spool Window (350) is not exacting, e.g., the Takeup Film Pad (355) might be at an oblique angle within the Takeup Spool Window (350). The determinative factor is the angle of the Transparent Film (105) to the Takeup Film Pad (355) such that the Takeup Film Pad (355) may be effective in removing debris from the Transparent Film (105).

Present in some embodiments but omitted from FIG. 6 are one or more fasteners for instances when fasteners might be used for affixing internal components or attaching together portions of the Takeup Module (300).

Figure 7:
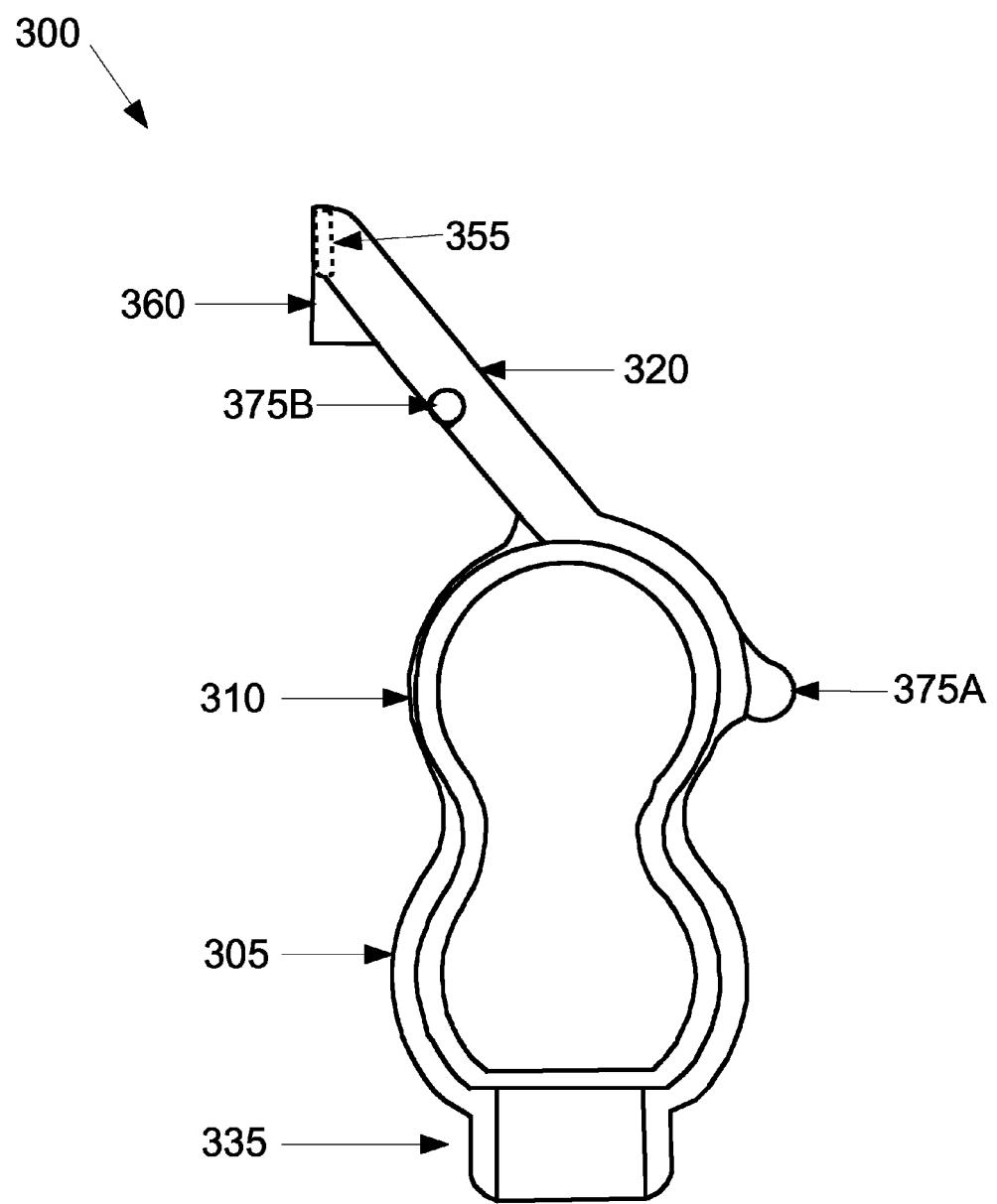
FIG. 7 shows a bottom view of an embodiment of the Takeup Module (300).

FIG. 7 shows a bottom view of an embodiment of the Takeup Module (300).

Shown in FIG. 7 are the Takeup Module (300), a Motor Compartment (305), a Takeup Spool Compartment (310), a Takeup Circuit Board Compartment (335), a Takeup Film Pad (355), a Takeup Goggle Pad (360), and a Takeup Spool Window Connector (375).

Present in some embodiments but omitted from FIG. 7 are one or more fasteners for instances when fasteners might be used for affixing internal components or attaching together portions of the Takeup Module (300).

Figure 8A:
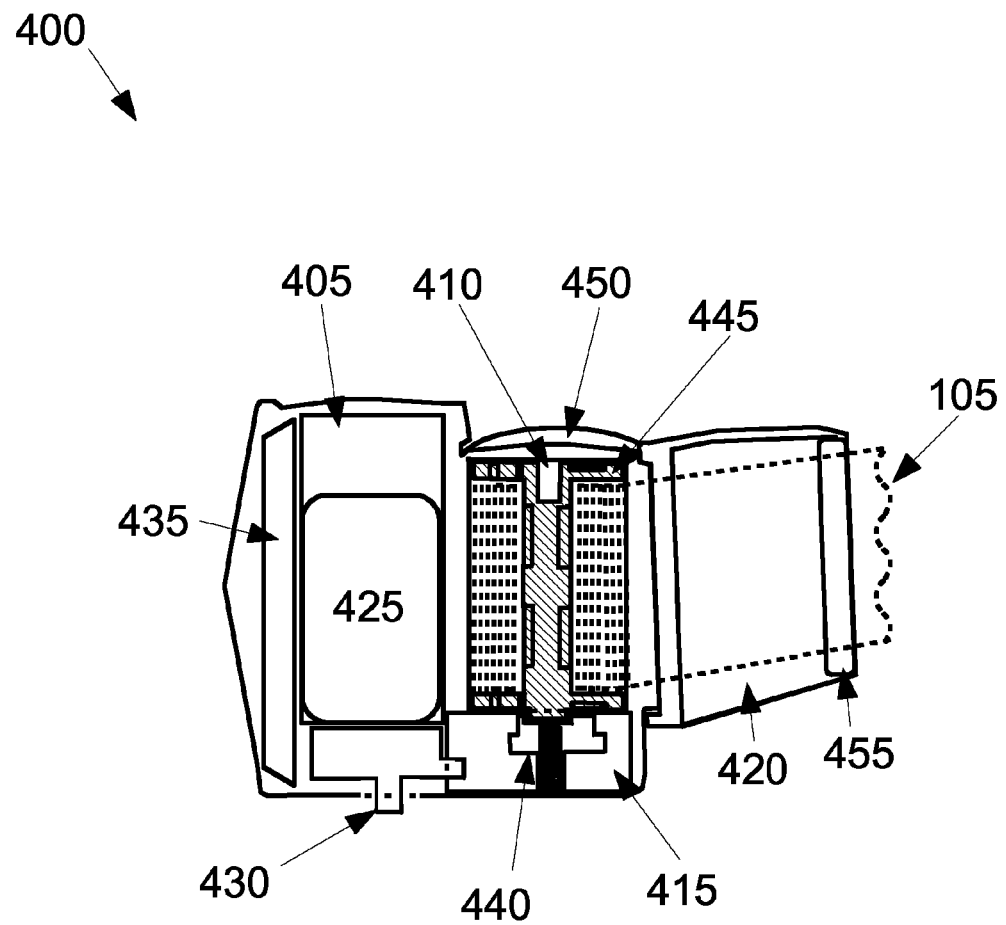
FIG. 8A shows an internal view of an embodiment of the RollOut Module (400).
Figure 8B:
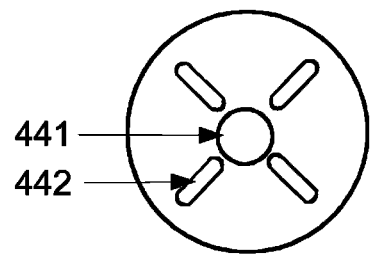
FIGS. 8B and 8C show a top and side view respectively of a Rollout Spool Tensioner (440).
Figure 8C:
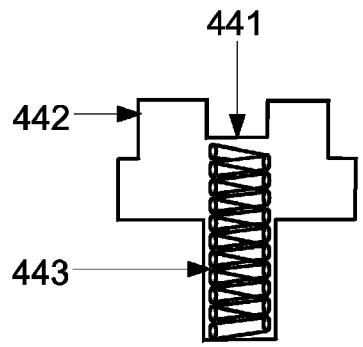

FIG. 8A shows an internal view of an embodiment of the Rollout Module (400). FIGS. 8b and 8c show a top and side view respectively of a Rollout Spool Tensioner (440). Shown in FIG. 8a are a Battery Compartment (405), a Rollout Spool Compartment (410), a Rollout Spool Gear Compartment (415), a Rollout Film Window (420), a Battery (425), a Battery Switch (430), a Rollout Circuit Board Compartment (435), a Rollout Spool Tensioner (440), a Rollout Spool (445), a Rollout Spool Window (450) and a Rollout Film Pad (455). Also shown is the Transparent Film (105) placed as it may be aligned for use in the Rollout Module (400).

The Battery Compartment (405) is configured to hold a Battery (425) for powering the OFF-ROAD ROLLING FILM VISION SYSTEM (100). The Battery Compartment (405) must be of sufficient size to hold a battery capable of operating the OFF-ROAD ROLLING FILM VISION SYSTEM (100) for a desired period of time. In some embodiments, the Battery Compartment (405) is sized for a 9V (a.k.a. PP3) battery. In some embodiments, the Battery Compartment (405) is sized for a plurality of AAA batteries. In some embodiments, the Battery Compartment (405) is sized for a plurality of AA batteries. In some embodiments, the Battery Compartment (405) has a translucent cover. In some embodiments, the Battery Compartment (405) has a transparent cover.

The Rollout Spool Compartment (410) is configured to hold and allow rotation of a Rollout Spool (445) for transferring a Transparent Film (105) from the Rollout Spool (445) to the Takeup Spool (345). In some embodiments, the Rollout Spool Compartment (410) is sized about the same as the Takeup Spool Compartment (310).

The Rollout Spool Gear Compartment (415) is beneath the Rollout Spool Compartment (410) to hold at least one Rollout Spool Tensioner (440) in direct contact with the Rollout Spool (445).

The Rollout Film Window (420), like the Takeup Film Window (320), provides multiple functions to the OFF-ROAD ROLLING FILM VISION SYSTEM (100). It provides a distance between the open air and the moving parts in the interior of the Rollout Module (400), thereby protecting them from the elements. In addition, the Rollout Film Window (420) serves as a steady travel path for the Transparent Film (105). In addition, when transparent, the Rollout Film Window (420) provides a user a view of and through the Transparent Film (105) as it enters the Rollout Module (400). Other details of the Rollout Film Window (420) will subsequently be shown and described.

The Battery (425) powers the Motor (325) for the OFF-ROAD ROLLING FILM VISION SYSTEM (100). In some embodiments, the Battery (425) is a 9V (a.k.a. PP3) battery. In some embodiments, the Battery (425) is a plurality of AAA batteries. In some embodiments, the Battery (425) is a plurality of AA batteries.

The Battery Switch (430) functions as an ON/OFF switch for the OFF-ROAD ROLLING FILM VISION SYSTEM (100) by electrically disconnecting the Battery (425) from other circuitry, e.g., the Takeup Circuit Board (370), which powers the Motor (325) in the Takeup Module (300). As shown in FIG. 8a, in some embodiments, the Battery Switch (430) extends outside the Rollout Module (400) for user access. In some embodiments, however, the Battery Switch (430) may be wholly internal, and perhaps engaged via wireless control, as described for the Control Module (200).

Some embodiments may have a Rollout Circuit Board Compartment (435), which might contain a Rollout Circuit Board (not shown), which might be used for wireless control of the Battery Switch (430), as from the Control Module (200).

The Rollout Spool Tensioner (440) secures the Rollout Spool (445) within the Rollout Spool Compartment (410) as well as allowing for a controlled rollout of the Transparent Film (105) from the Rollout Spool Compartment (410). The Rollout Spool Tensioner (440) allows the Rollout Spool (445) to freely rotate yet without over-spin, which might jam the OFF-ROAD ROLLING FILM VISION SYSTEM (100).

As shown in FIG. 8B, the Rollout Spool Tensioner (440) comprises a Rollout Spool Tensioner Spool Countersink (441) and Rollout Spool Tensioner Spool Latch (442) capable of engaging a Rollout Spool (445) for applying tension to the Rollout Spool (445).

As shown in FIG. 8C, the Rollout Spool Tensioner (440) comprises in some embodiments, a Rollout Spool Tensioner Spring (443). The Rollout Spool Tensioner Spring (443) may be a coil spring (shown), a leaf spring, or any device for allowing for a controlled rollout of the Transparent Film (105) from the Rollout Spool Compartment (410). The term 'spring' is for reference use only, as any other device capable of allowing for a controlled rollout of the Transparent Film (105) from the Rollout Spool Compartment (410) may be used.

Also shown in FIG. 8A is a Rollout Spool (445) which provides storage and unspooling of the Transparent Film (105) for Rollout Module (400) of the OFF-ROAD ROLLING FILM VISION SYSTEM (100). In most embodiments, the Rollout Spool (445) is the same as the Takeup Spool (345). However, as the Transparent Film (105) is subject to damage in use, and wrapping distinctions in unspooling and spooling mitigate easy re-use of the Transparent Film (105), the Rollout Spool (445) is not needed to be the same as the Takeup Spool (345). The Rollout Spool (445) must fit within the Rollout Spool Compartment (410), hold a desired stock of the Transparent Film (105), and unspool without jamming.

In some embodiments, a Rollout Spool Window (450) is attached to the Rollout Module (400) atop the Rollout Spool Compartment (410) to provide a view of the Rollout Spool (445). This view of the Rollout Spool (445) grants a visible indication of how much transparent film is present on the Rollout Spool (445). In some embodiments, the Rollout Spool Window (450) is made of transparent plastic. In some embodiments, the Rollout Spool Window (450) is made of glass. In some embodiments, the Rollout Spool Window (450) is made of a non-transparent material interspersed with a transparent material. The Rollout Spool Window (450) may be partially transparent, or may be opaque in part and transparent in part, (as by a diametrical slot), or may be wholly opaque, for instances when other techniques might be used to determine the amount of Transparent Film (105) on the Rollout Spool (445).

In some embodiments, a Rollout Film Pad (455) is present to remove debris from the Transparent Film (105) as the Transparent Film (105) exits the Rollout Module (400). The Rollout Film Pad (455) may act as a knife to scrap debris from the Transparent Film (105), or as a blotter to absorb debris from the Transparent Film (105), or both. The Rollout Film Pad (455) may be any material suitable, including soft materials such as paper, natural organic materials such as rubber, artificial organic materials such as foam, plasticized PVC, or harder materials including rigid plastics, wood, or metal.

Present in some embodiments but omitted from FIG. 8A are one or more fasteners for instances when fasteners might be used for affixing internal components or attaching together portions of the Takeup Module (300).

Figure 9:
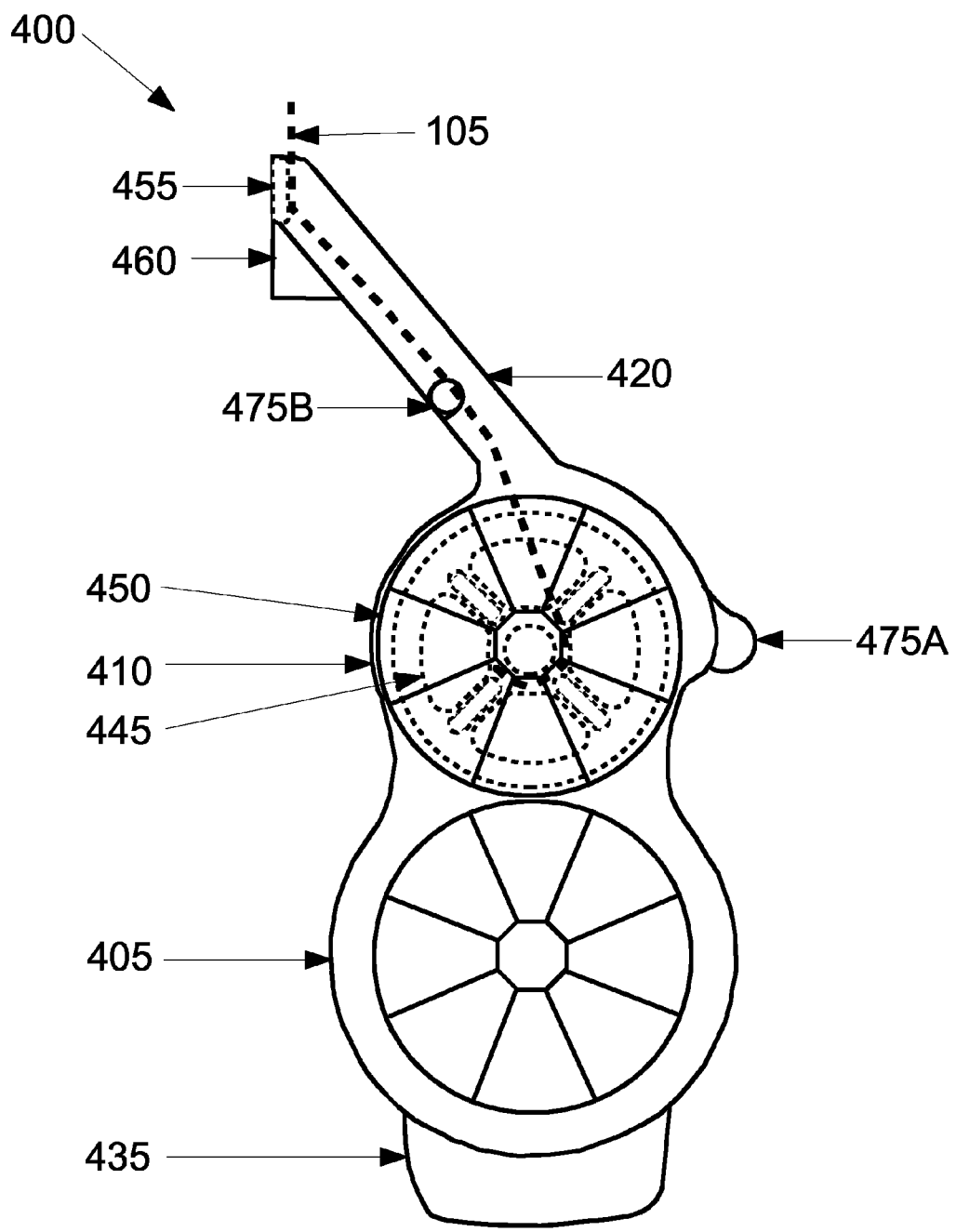
FIG. 9 shows a top view of an embodiment of the Rollout Module (400).

FIG. 9 shows a top view of an embodiment of the Rollout Module (400). Shown in FIG. 9 are the Battery Compartment (405), a Rollout Spool Compartment (410), the Rollout Film Window (420), the optional Rollout Circuit Board Compartment (435), the Rollout Spool Window (450), the Rollout Film Pad (455), the Rollout Goggle Pad (460) and the Rollout Film Window Hinge-Connector (475A and 475B).

As shown in FIG. 9, the Rollout Spool Window (450) rests above the Rollout Spool (445) so that a person may see how much Transparent Film (105) remains on the Rollout Spool (445). Though shown as wholly transparent in entirety, the Rollout Spool Window (450) may be partially transparent, or may be opaque in part and transparent in part, (as by a diametrical slot), or may be wholly opaque, for instances when other techniques might be used to determine remaining spool capacity.

FIG. 9 also presents a view of the Transparent Film (105) and the Rollout Film Pad (455) within the Rollout Spool Window (450) as the Transparent Film (105) might be aligned within the Rollout Film Pad (455) and wrapped around the Rollout Spool (445). The particular alignment of the Rollout Film Pad (455) within the Rollout Spool Window (450) is not exacting, e.g., the Rollout Film Pad (455) might be at an oblique angle within the Rollout Spool Window (450). The determinative factor is the angle of the Transparent Film (105) to the Rollout Film Pad (455) such that the Rollout Film Pad (455) may be effective in removing debris from the Transparent Film (105).

The Rollout Spool Window Hinge-Connector (475A and 475B) aids in proper placement of the transparent film by allowing the user to move the Rollout Film Window (420) to align the Transparent Film (105) within it. In some embodiments, the Rollout Spool Window Hinge-Connector (475A and 475B) are pins and slots. In some embodiments, the Rollout Spool Window Hinge-Connector (475A and 475B) are a hinge and a pin.

Figure 10:
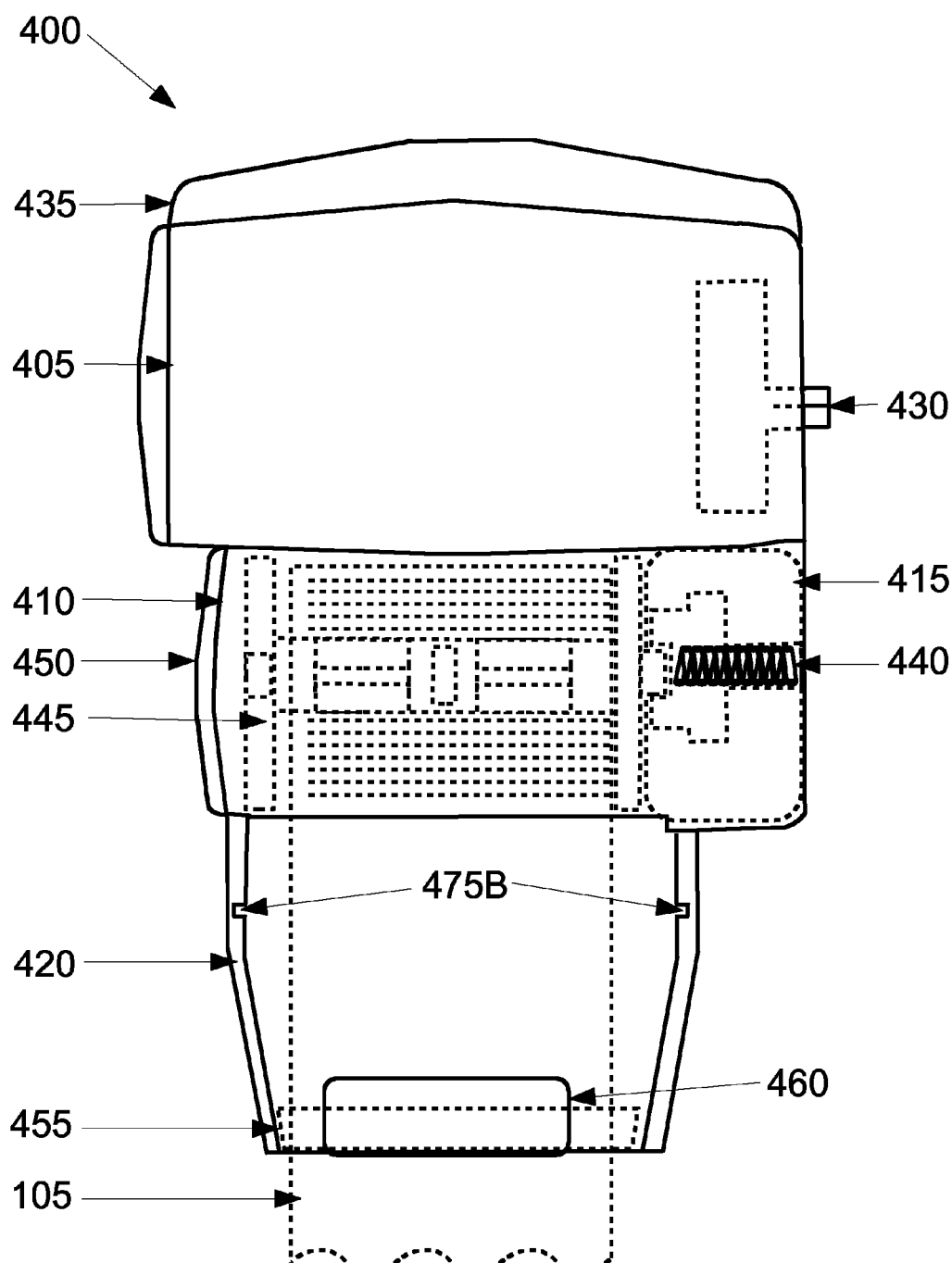
FIG. 10 shows an back view of a embodiment of the Rollout Module (400).

FIG. 10 shows a back view of a embodiment of the Rollout Module (400).

Shown in FIG. 10 are the Battery Compartment (405), a Rollout Spool Compartment (410), the Rollout Film Window (420), a Battery Switch (430), an optional Rollout Circuit Board Compartment (435), a Rollout Spool Tensioner (440), the Transparent Film (105) as it may be spooled on a Rollout Spool (445) and aligned for use in the Rollout Module (400), a Rollout Spool Window (450) and a Rollout Film Pad (455), the Rollout Goggle Pad (460) and a portion of the Rollout Film Window Hinge-Connector (475B).

Some embodiments comprise a Rollout Circuit Board Compartment (435) that might be used to replace or augment the Takeup Circuit Board Compartment (335).

As shown in FIG. 10, the Rollout Spool (445) is reversely aligned within the Rollout Module (400) from the Takeup Spool (345) in the Takeup Module (300). This transposition of the Rollout Spool (445) allows the OFF-ROAD ROLLING FILM VISION SYSTEM (100) to use the same spool for Rollout and Takeup, but with better tension control on the film.

Figure 11:
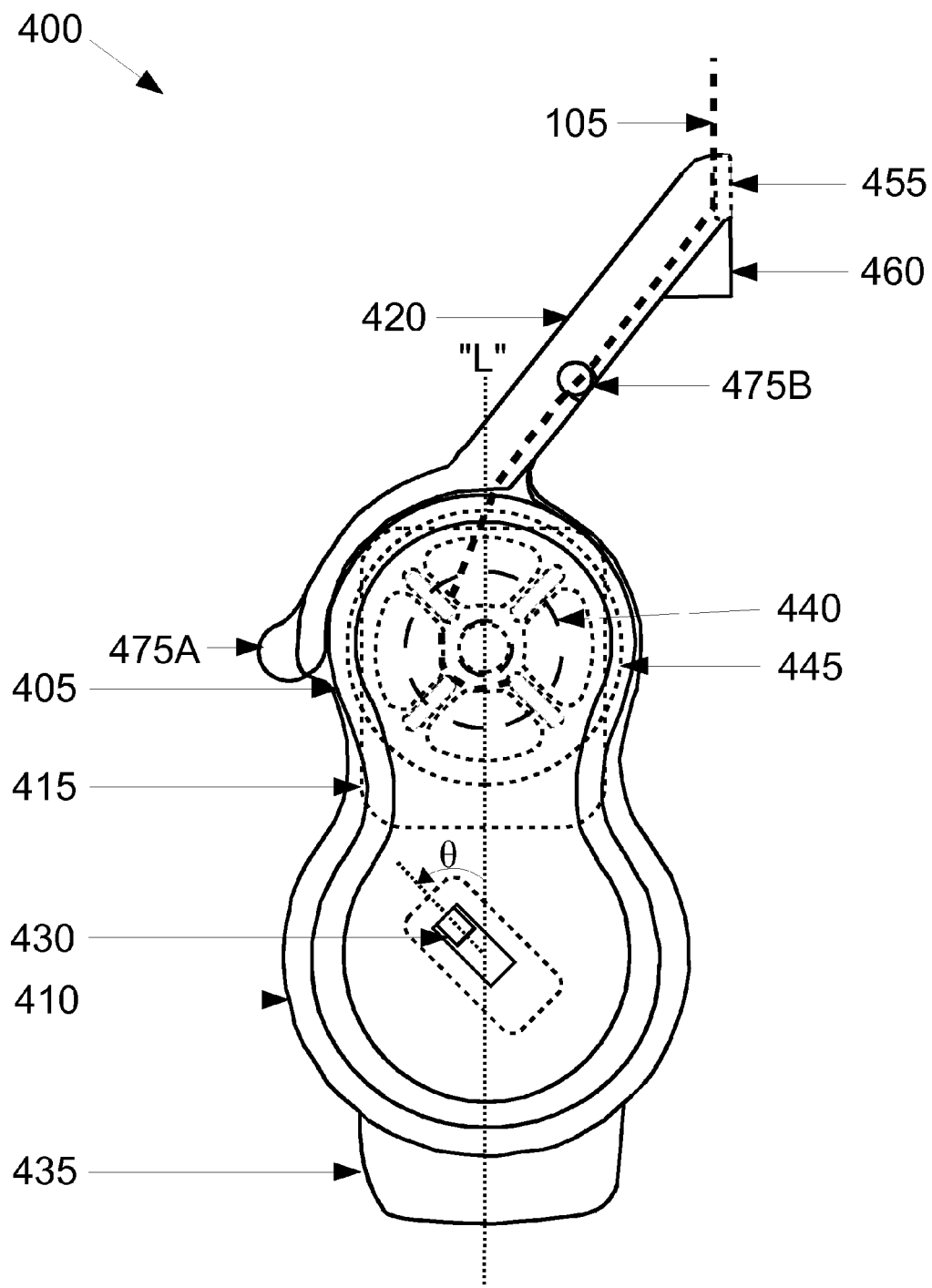
FIG. 11 shows a bottom view of an embodiment of the Rollout Module (400).

The Battery Switch (430) is described in FIG. 11.

The Rollout Spool Tensioner (440) is described in FIG. 8B and FIG. 8C.

FIG. 11 shows a bottom view of an embodiment of the Rollout Module (400). Shown in FIG. 11 are the Battery Compartment (405), a Rollout Spool Compartment (410), an outline of the Rollout Spool Gear Compartment (415), the Rollout Film Window (420), a Battery Switch (430), an optional Rollout Circuit Board Compartment (435), an outline of the Rollout Spool Tensioner (440) attached to the Rollout Spool (445), with the Transparent Film (105) as it may be partially spooled on a Rollout Spool (445) and aligned for use in the Rollout Module (400), a Rollout Film Pad (455), the Rollout Goggle Pad (460) and the Rollout Film Window Hinge-Connector (475A and 475B).

In some embodiments, the Battery Switch (430) has an oblique angle ("θ") to a longitudinal axis ("L") of the Rollout Module (400). This angled configuration may be easier for some users to switch the Battery (425) between "ON" and "OFF" from the circuit of the OFF-ROAD ROLLING FILM VISION SYSTEM (100).

Present in some embodiments but omitted from FIG. 11 are one or more fasteners for instances when fasteners might be used for affixing internal components or attaching together portions of the Takeup Module (300).

FIGS. 12A, 12B, 12C, 12D and 12E show embodiments of a Spool (500).

Figure 12A:
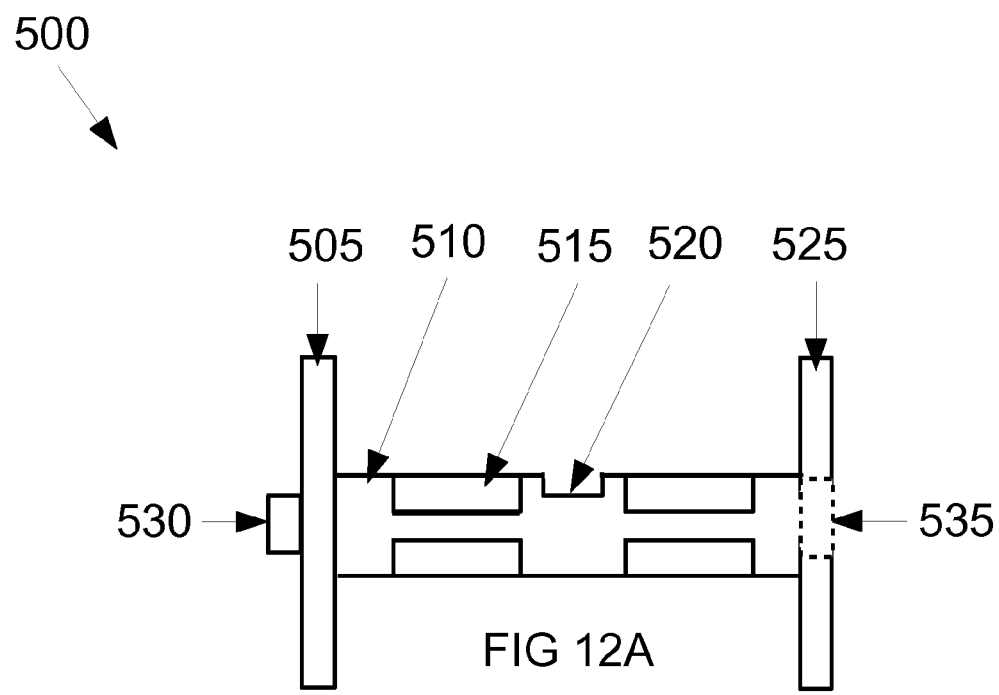
Figure 12B:
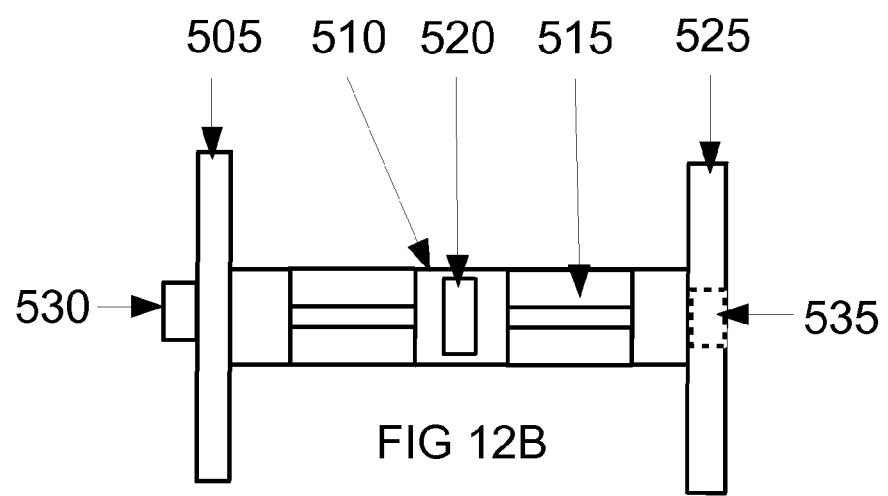

Shown in FIG. 12A and FIG. 12B are the Spool (500) and its structures a Spool Alignment Tab Wheel (505), a Spool Ribbed Shaft (510), a Rib Quarter Section Cutout (515), a Midsection Cutout (520), a Spool Alignment Slot Wheel (525), a Spool Alignment Tab (530), and a Spool Alignment Slot (535).

The Spool (500) may be used for the Takeup Spool (345), the Rollout Spool (445), or for both. In a typical embodiment, the Spool (500) would be used for both the Takeup Module (300) and the Rollout Module (400) so that a spent Rollout Spool (445) might be used as a Takeup Spool (345).

The Spool (500) may be made of any material of sufficient strength to withstand the forces of being turned by the Motor (325), the Motor Gearbox (330) and the at least one Takeup Spool Gear (340), as well as the additional forces due to the environmental conditions typically associated with off-road recreation, including temperatures above 100 F and below 40 F.

The Spool (500) may be made of acrylonitrile butadiene styrene (ABS), which has sufficient impact resistance, toughness and thermal stability to meet these conditions. Other plastics may be used, though the Spool (500) may suffer from fatigue failure or thermal failure, or may be more expensive.

The Spool (500) may be made of natural materials, including aluminum and iron alloys such as steel, or other metals. Once again, cost may be a factor, as may weight.

The Spool Alignment Tab Wheel (505) functions to align the Transparent Film (105) within the Spool (500) and is a base for other features of the Spool (500).

The Spool Ribbed Shaft (510) provides two primary functions for the Spool (500). First, the Spool Ribbed Shaft (510) supports the Spool (500) within the Takeup Spool Compartment (310) and the Rollout Spool Compartment (410). In addition the Spool Ribbed Shaft (510) maintains a fixed distance between the Spool Alignment Tab Wheel (505) and the Spool Alignment Slot Wheel (525) so the Transparent Film (105) does not bind or shift.

The Rib Quarter Section Cutout (515) provides longitudinal strength to the Spool (500) by providing ribbing that lessens the opportunity that the Spool Ribbed Shaft (510) might flex.

Some embodiments may comprise a Midsection Cutout (520) as a feature of the Spool (500). Injection molded embodiments of the Spool (500) may find the Midsection Cutout (520) useful as a gate location.

The Spool Alignment Slot Wheel (525 functions) to align the Transparent Film (105) within the Spool (500) and is a base for other features of the Spool (500).

The Spool Alignment Tab (530) functions to align the Spool (500) within the Takeup Spool Compartment (310) and the Rollout Spool Compartment (410). In a preferred embodiment, the Spool Alignment Tab (530) is a round stub atop the Spool Ribbed Shaft (510) and aligned at the center of the Spool Alignment Tab Wheel (505). With this embodiment, the Spool (500) is likely to stay centered within the Takeup Spool Compartment (310) and the Rollout Spool Compartment (410). FIG. 12C shows another view of the Spool Alignment Tab (530).

The Spool Alignment Slot (535), like the Spool Alignment Tab (530) functions to align the Spool (500) within the Takeup Spool Compartment (310) and the Rollout Spool Compartment (410). In a preferred embodiment, the Spool Alignment Slot (535) is a rectangular oval within the Spool Ribbed Shaft (510) and is aligned at the center of the Spool Alignment Slot Wheel (525). With this embodiment, the Spool (500) is likely to stay centered within the Takeup Spool Compartment (310) and the Rollout Spool Compartment (410). FIG. 12D shows another view of the Spool Alignment Slot (535).

FIG. 12C shows a face-on view of the Spool Alignment Tab Wheel (505). Shown in FIG. 12C are the Spool (500) and its structures the Spool Alignment Tab Wheel (505), the Spool Alignment Tab (530), a Plurality of Wheel Cutouts (540) and a Plurality of Wheel Slots (545).

The Plurality of Wheel Cutouts (540) function to reduce sink and warping in injection molded embodiments of the Spool (500), while reducing weight and thus the energy needed to turn the Spool (500) in heavier embodiments of the Spool (500).

The Plurality of Wheel Slots (545) mate with the Rollout Spool Tensioner Spool Latch (442) of the Rollout Spool Tensioner (440) to assure proper tension on the Rollout Spool (445). The Plurality of Wheel Slots (545) also reduce sink and warping in injection molded embodiments of the Spool (500), and may be used as part of a counting system for showing the length of Transparent Film (105) used or remaining for use in the OFF-ROAD ROLLING FILM VISION SYSTEM (100).

FIG. 12D shows a face-on view of the Spool Alignment Slot Wheel (525). Shown in FIG. 12D are the Spool (500) and its structures the Spool Alignment Slot Wheel (525), the Spool Alignment Slot (535) and a Plurality of Wheel Cutouts (540) and a Plurality of Wheel Slots (545). With the exception of the Spool Alignment Tab (530) and the Spool Alignment Slot (535), the Spool Alignment Tab Wheel (505) and the Spool Alignment Slot Wheel (525) are nearly identical, which aids in providing rotational balance to the Spool (500).

As shown in FIG. 12C, the Spool Alignment Tab (530) is a structure of the Spool Alignment Tab Wheel (505), while as shown in FIG. 12D, the Spool Alignment Slot (535) is a structure of the Spool Alignment Slot Wheel (525). In some embodiments, the locations of the Spool Alignment Tab (530) and the Spool Alignment Slot (535) may be switched.

FIG. 12E shows a side view of the Spool (500) to show the relative locations of the structures of the Spool (500). Shown in FIG. 12E are the Spool (500) and its structures the Spool Alignment Tab Wheel (505), the Spool Ribbed Shaft (510), the Rib Quarter Section Cutout (515), the Midsection Cutout (520), the Spool Alignment Slot Wheel (525), the Spool Alignment Slot (535), and the Plurality of Wheel Cutouts (540) and the Plurality of Wheel Slots (545).

Figure 13:
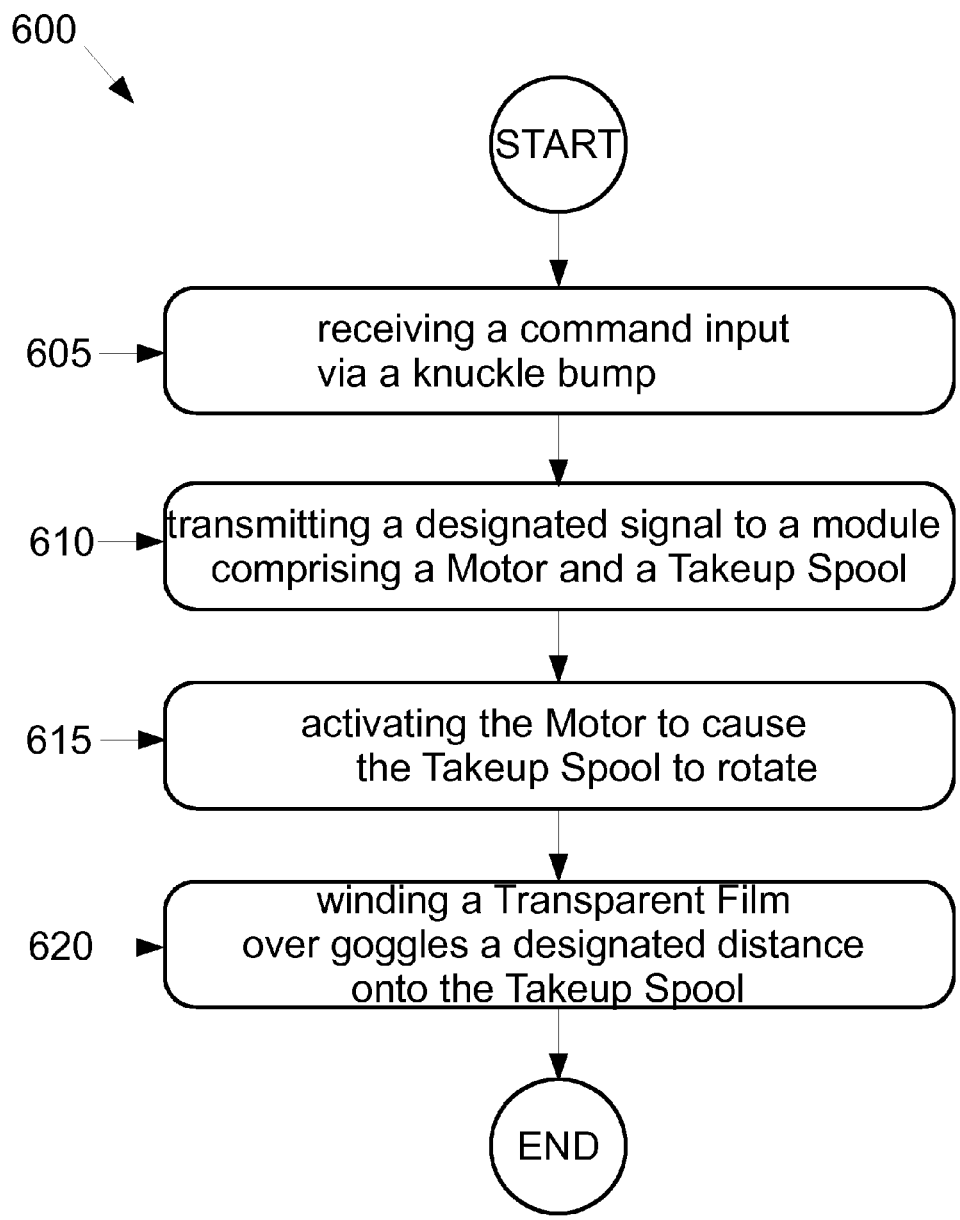
FIG. 13 shows a method of maintaining clear vision with goggles.

FIG. 13 shows a method of maintaining clear vision with goggles.

The method comprises the steps of:

Step 610: receiving a command input via a knuckle bump,

Step 620: transmitting a designated signal to a module comprising a Motor and a Takeup Spool, Step 630: activating the Motor to cause the Takeup Spool to rotate, and Step 640: winding a Transparent Film over goggles a designated distance onto the Takeup Spool.

These descriptions and drawings are embodiments and teachings of the disclosure. All variations are within the spirit and scope of the disclosure. This disclosure is not to be considered as limiting the claims to only the embodiments illustrated or discussed. Certain changes can be made in the subject matter without departing from the spirit and the scope of this invention. It is realized that changes are possible within the scope of this invention and it is further intended that each structure or element recited in any of the claims is to be understood as referring to all equivalent structure or elements. The following claims are intended to cover the invention as broadly as possible in whatever form it may be used.

What is claimed is:

1. An off-road rolling film vision system comprising a controller module (200), a takeup module (300), and a rollout module (400)
wherein the controller module (200) comprises a command input (205), a controller process module (210), a command transmitter (215), and a power supply (220),
wherein the controller module (200) has at least one button on a lateral face of the controller module (200) configured to accept a knuckle bump for controlling a motor (325) in the takeup module (300) to move a transparent film (105) across goggles with the at least one button configured on a lateral face of the controller module (200) to be adjacent to user's metacarpophalangeal joint, and
the takeup module (300) comprises a motor compartment (305), a takeup spool compartment (310), a takeup spool gear compartment (315), and a takeup film window (320) wherein the takeup spool compartment (310) and the takeup film window (320) are separate structures with the takeup film window (320) configured as a steady travel path for the transparent film (105) and with a transparent takeup spool window (350) to provide a view of a takeup spool (345) within the takeup module (300).

2. The off-road rolling film vision system of claim 1 wherein the at least one button configured on a lateral face of the controller module (200) to accept a knuckle bump is configured to be adjacent to a user's metacarpophalangeal index finger joint.

3. The off-road rolling film vision system of claim 1 wherein the at least one button configured on a lateral face of the controller module (200) to accept a knuckle bump is configured to be adjacent to a user's metacarpophalangeal thumb joint.

4. The off-road rolling film vision system of claim 1 wherein the power supply (220) comprises a battery.

5. The off-road rolling film vision system of claim 1 wherein the command transmitter (215) is capable of communicating with the takeup module (300) via infra-red technology.

6. The off-road rolling film vision system of claim 1 wherein the command transmitter (215) is capable of communicating with the takeup module (300) via radio technology.

7. The off-road rolling film vision system of claim 1 wherein the command transmitter (215) is capable of communicating with the takeup module (300) via a wireless communication for exchanging data over short distances using short-wavelength ultrahigh frequency radio waves from 2.4 to 2.485 GHz and capable of connecting up to seven devices.

8. The off-road rolling film vision system of claim 1 wherein the command transmitter (215) is capable of communicating with the takeup module (300) via a wireless communication for exchanging small data packets over short distances at up to 100 kilobits per second using a source-routed mesh network architecture.

9. The off-road rolling film vision system of claim 1 wherein the command transmitter (215) is capable of communicating with the takeup module (300) via a wireless communication for exchanging data over short distances following the IEEE 802.15.4 standard and using low-power low-bandwidth line-of-sight transmissions at up to 250 kbits per second.

10. The off-road rolling film vision system of claim 1 wherein the takeup module (300) further comprises a takeup circuit board compartment (335).

11. The off-road rolling film vision system of claim 1 wherein the takeup module (300) further comprises a takeup film pad (355).

12. The off-road rolling film vision system of claim 1 further comprising a motor (325) and a motor gearbox (330) to convert a native speed and torque of the motor (325) to a proper speed and torque for the takeup spool (345) to takeup the transparent film (105).

13. The off-road rolling film vision system of claim 1 wherein the takeup module (300) further comprises a takeup goggle pad (360) located exterior to the takeup film window (320) to mitigate movement and absorb activity vibration to aid maintaining the takeup module (300) in place.

14. The takeup film window (320) of claim 1 further comprising a spool tab slot (380) within the takeup spool window (350) of the takeup spool compartment (310) configured to provide passage for a spool alignment tab (530) of a takeup spool (345).

15. The off-road rolling film vision system of claim 1 wherein the rollout module (400) comprises a battery compartment (405), a rollout spool compartment (410), a rollout spool gear compartment (415), a rollout film window (420), a battery switch (430), and a rollout spool tensioner (440).

16. The off-road rolling film vision system of claim 15 wherein the rollout module (400) further comprises a transparent rollout spool window (450) to provide a view of a rollout spool (445) within the rollout module (400).

17. The off-road rolling film vision system of claim 15 wherein the rollout film window (420) is transparent to provide a view of and through a transparent film (105) within the rollout module (400).

18. The off-road rolling film vision system of claim 15 wherein the rollout module (400) further comprises a rollout circuit board compartment (435).

19. The off-road rolling film vision system of claim 15 wherein the rollout module (400) further comprises a rollout goggle pad (460) located exterior to the rollout film window (420).

20. The off-road rolling film vision system of claim 15 wherein the battery switch (430) has an oblique angle (θ) to a longitudinal axis (L) of the rollout module (400).

21. The off-road rolling film vision system of claim 15 wherein the rollout spool tensioner (440) comprises a rollout spool tensioner spool countersink (441) and a rollout spool tensioner spool latch (442) capable of engaging a rollout spool (445) for applying tension to the rollout spool (445).

* * * * *